(12) United States Patent
Martin et al.

(10) Patent No.: US 7,348,182 B2
(45) Date of Patent: *Mar. 25, 2008

(54) DIRECTED MICROWAVE CHEMISTRY

(75) Inventors: Mark T. Martin, Rockville, MD (US); Richard Saul, Gaithersburg, MD (US)

(73) Assignee: Mirari Biosciences, Inc., Rockville, MD (US)

(*) Notice: Subject to any disclaimer, the term of this patent is extended or adjusted under 35 U.S.C. 154(b) by 591 days.

This patent is subject to a terminal disclaimer.

(21) Appl. No.: 10/234,092

(22) Filed: Sep. 5, 2002

(65) Prior Publication Data

US 2003/0082633 A1    May 1, 2003

Related U.S. Application Data

(63) Continuation-in-part of application No. 09/968,517, filed on Oct. 2, 2001.

(60) Provisional application No. 60/237,192, filed on Oct. 3, 2000.

(51) Int. Cl.
*G01N 33/543* (2006.01)
*C12M 1/00* (2006.01)

(52) U.S. Cl. ........... 436/518; 436/173; 436/50; 436/51; 436/526; 436/806; 435/4; 435/6; 435/7.1; 435/287.1; 435/287.2; 422/82.01; 427/2.1

(58) Field of Classification Search ........... 436/518, 436/173, 806, 350, 51, 526, 149; 435/4, 435/6, 7.1, 287.1, 287.2; 427/2.1; 422/82.01
See application file for complete search history.

(56) References Cited

U.S. PATENT DOCUMENTS

| | | | |
|---|---|---|---|
| 3,455,842 A | 7/1969 | Cornelius et al. | |
| 3,839,175 A | 10/1974 | Keyes | |
| 4,340,672 A | 7/1982 | Kondo et al. | 435/45 |
| 4,575,485 A | 3/1986 | Sizto et al. | 435/7 |
| 4,822,492 A | 4/1989 | Chao et al. | |
| 4,822,566 A | 4/1989 | Newman | |
| 4,880,752 A * | 11/1989 | Keck et al. | 435/7.72 |
| 5,350,686 A | 9/1994 | Jhingan | 435/173.2 |
| 5,427,779 A * | 6/1995 | Elsner et al. | 424/78.17 |

(Continued)

FOREIGN PATENT DOCUMENTS

| | | |
|---|---|---|
| EP | 0 487 091 A2 | 5/1992 |
| GB | 1 363 526 | 8/1974 |

OTHER PUBLICATIONS

Abati, A. & Liotta, L.A., "Looking Forward in Diagnostic Pathology," (1996) Cancer 78, 1-3.
Baziard, Y & Gourdenne, A, Cross-linking Under Microwaves (2.45 GHz) of Aluminum Powder-Epoxy Resin Composites I. Electrical Power Dependence (1988) Eur. Polym. J. 24, 873.
Boon, M.E. & Kok, L.P. (1989) in Microwave Cookbook of Pathology, p. 17, Coulomb Press, Leiden.
Boon, M.E. "Microwave Cookbook of Pathology," Coulomb Press Leyden 1989, 1-219.

(Continued)

*Primary Examiner*—Long V. Le
*Assistant Examiner*—Pensee T. Do
(74) *Attorney, Agent, or Firm*—Jenkins, Wilson, Taylor & Hunt, P.A.

(57) ABSTRACT

The present invention concerns a novel means by which chemical preparations can be made. Reactions can be accelerated on special chips using microwave energy. The chips contain materials that efficiently absorb microwave energy causing chemical reaction rate increases. The invention is important in many small scale chemical transformations including those used in protein chemistry and in combinatorial chemistry.

15 Claims, 9 Drawing Sheets

U.S. PATENT DOCUMENTS

| | | | | |
|---|---|---|---|---|
| 5,451,428 | A | * | 9/1995 | Rupp .................. 427/2.12 |
| 5,478,748 | A | * | 12/1995 | Akins et al. ............... 436/86 |
| 5,496,701 | A | * | 3/1996 | Pollard-Knight ......... 435/7.4 |
| 5,689,008 | A | * | 11/1997 | Satyapal et al. .......... 568/403 |
| 5,780,578 | A | | 7/1998 | Mashelkar et al. ....... 528/327 |
| 5,869,349 | A | | 2/1999 | Lin et al. |
| 5,911,941 | A | | 6/1999 | Rokhvarger et al. ..... 264/432 |
| 5,922,537 | A | | 7/1999 | Ewart et al. .............. 435/6 |
| 5,985,356 | A | | 11/1999 | Schultz et al. ............ 427/8 |
| 6,011,247 | A | | 1/2000 | Grillo et al. ............ 219/686 |
| 6,180,415 | B1 | | 1/2001 | Schultz et al. .......... 436/518 |

OTHER PUBLICATIONS

Borchart, A. & Still, W.C., Synthetic Receptor Binding Elucidated with an Encoded Combinatatorial Library, (1994) J. Am. Chem. Soc. 116, 373.

Borman, S., "Combinatorial Chemistry," (2001) Chem Engineer. News Aug. 27, 2001, pp. 49-58.

Bose, A.K. et al. "MORE Chermistry in a Microwave," (1997) CHEMTECH 27(9), 18-25.

Bowie, A.R., Sanders, M.G., & Worsfold, P.J. (1996), "Analytical Applications of Liquid Phase Chemiluminescence Reactions—A Review," J. Biolumin. Chemilumin. 11, 61-90.

Bram, G. et al. "Alkylation of Potassium Acetate in "Dry Media" Thermal Activation In Commercial Microwave Ovens," (1990) Tetrahedron 46, 5167.

Bram, G., Loupy, A., Majdoub, M., and Petit, A., "Anthraquinone Microwave-Induced Synthesis In Dry Media in Domestic Ovens," (1991) Chem. Ind. 396.

Breslow, R. et al. (1983), "Optimization of Metallocene Substrates for Beta-Cyclodextrin Reactions," J. Am. Chem. Soc. 105, 2739.

Buffler, C.R. & Risman, P.O. (1996), "Microwave Processing of Materials," Mat. Res. Soc. Symp. Proc. 430, 85.

Burow, M. & Minoura, N., "Molecular Imprinting: Synthesis of Polymer Particles with Antibody-like Binding Characteristics for Glucose Oxidase," (1996) Biochem. Biophys. Res. Commun. 227, 419.

Bystrom, S.E. et al., "Selective Reduction of Steroid 3- and 17-Ketones Using LiAlH4 activated Template Polymers," (1993) 115, 2081.

Cooper, C.S., "Applications of Microarray Technology in Breast Cancer Research," (2001) Breast Cancer Res. 3, 158-175.

Dai, S. et al., "Imprint Coating: A Novel Synthesis of Selective Functionalized Ordered Mesoporous Sorbents," (1999) Angew. Chem. Int. Ed. 38, 1235.

Dickert, FL & Thierer S, "Molecularly Imprinted Polymers for Optichemical Sensors," (1996) Adv. Mater. 8, 987.

Dolle, R.E., "Comprehensive Survey of Combinatorial Library Synthesis: 1999," (2000) J. Comb. Chem. 2, 383-433.

Draghici, S. et al., "Experimental Design, Analysis of Variance and Slide Quality assessment in Gene Expression Arrays," (2001) Curr. Opin. Drug Discov. Dev. (2001) 4, 332-337.

Fodor, S.P.A. et al. "Multiplexed Biochemical Assays With Biological Chips," (1993) Nature 364, 555-556.

Folkman, J. "Angiogenesis and Angiogenesis Inhibition: An Overview,"(1997) EXS 79, 1-8.

Freeman, W.M. et al. "Quantitative RT-PCR: Pitfalls and Potential," Walker, S.J., & Vrana, K.E. (1999) BioTechniques 26, 112-125.

Gabriel, C. et al. "Dielectric Parameters Relevant to Microwave Dielectric Heating," (1998) Chem. Soc. Rev. 27, 213-224.

Gallop, M.A. et al., "Applications of Combinatorial Technologies to Drug Discovery. 1. Background and Peptide Combinatorial Libraries," (1994) J. Med. Chem. 37(9), 1233-1251.

Glad et al., "Use of Silane Monomers for Molecular Imprinting and Enzyme Entrapment in Polysiloxane-Coated Porous Silica," (1985) J. Chromatogr. 347, 11.

Gordon, E.M. et al., "Applications of Combinatorial Technologies to Drug Discovery. 2. Combinatorial Organic Synthesis, Library Screening Strategies and Future Directions," (1994) J. Med. Chem. 37(10), 385-401.

Gu, W. et al., "Photo-Fries Reactions of 1-Naphthyl Esters in Cation-Exchanged Zeolite Y and Polyethylene Media," (1999) J. Am. Chem. Soc. 121, 9467.

Harkin, D.P., "Uncovering Functionally Relevant Signalling Pathways Using Microarray-Based Expression Profiling," (2000) Oncologist 5, 501-7.

Hasted, J.B., "Aqueous Dielectrics," (1973) chapman & Hall, London, 1-255.

Hergenrother, P.J. et al. "Small-Molecule Microarrays: Covalent Attachment and Screening of Alcohol-Containing Small Molecules on Glass Slides," (2000) J. Amer. Chem. Soc. 122, 7849-7850.

Hilpert, K. et al. "Anti-c-myc Antibody 9E10: Epitope Key Positions and Variability Characterized Using Peptide Spot Synthesis on Cellulose," (2001) Prot. Engineer. 14, 803-806.

Holzworth, A. et al., "Enhanced Microwave Heating of Nonpolar Solvents by Dispersed Magnetic Nanoparticles," Ind. Eng. Chem. Res. (1998) 37, 2701.

Huhmer, A.F.R. and Landers, J.P, "Noncontact Infrared-Mediated Thermocycling for Effective Polymerase Chain Reaction Amplification of DNA in Nanoliter vol.," (2000) Anal. Chem. 72, 5507-5512.

Jacobs, J.W. et al. "Combinatorial Chemistry—Applications of Light-Directed Chemical Synthesis," (1994) Trends Biotechnol. 12, 19-26.

Jiang, P. et al., "Template-Directed Preparation of Macroporous Polymers with Oriented and Crystalline Arrays of Voids," (1999) J. Am. Chem. Soc. 121, 11630.

Jin, Q. et al., "Application of Microwave Techniques in analytical Chemistry," (1999) Trends Anal. Chem. 18, 479-484.

Johnson, B., "All's Well That Ends Well: A Profile of Specialty Microwell Plates," (1999) The Scientist 13, 16.

Jones, K.D., "Membrane Immobilization of Nucleic Acids: Part 1: Substrates," IVD (2001) Technology 7(6) 50-54.

Kappe, C.O. "Speeding Up Solid-Phase Chemistry By Microwave Irradiation: A Tool for High-Throughput Synthesis," (2001) American Laboratory 23, 13-19.

Kappe, C.O., "High-Speed Combinatorial Synthesis Utilizing Microwave Irradiation," (2002) Curr. Opin. Chem. Biol. 6, 314-320.

Kempe et al., "An Approach Towards Surface Imprinting Using the Enzyme Ribonuclease A," (1995) J. Mol. Recog. 8, 35.

Kidwai, M., Kohli, S., Saxena, R.K., Gupta, R., and Bardoo, S., "A Novel Enzymatic Synthesis of 2-substituted Naphtho[2,1-b]-pyran-3-ones Using Microwaves," (1998) Ind. J. Chem. 37B, 963.

Korbel, G.A. et al., "Reaction Microarrays: A Method for Rapidly Determining the Enantiomeric Excess of Thousands of Samples," (2001) J. Am. Chem. Soc. 123, 361-362.

Kramer, A. et al., Synthesis and Screening of Peptide Libraries on Continuous Cellulose Membrane Supports, (1998) Methods Molec. Biol. 87, 25-39.

Kricka, L.J., "Nucleic Acids Detection Technologies—Labels Strategies, and Formats," (1999) Clin. Chem. 45, 453-8.

Krishnan, T.R. & Ibraham, I., "Solid-Phase Extraction Techniques for the Analysis of Biological Samples," (1994) J. Pharm. Biomed. Anal. 12, 287-294.

Kubrakova, I. V., "Effect of Microwave Radiation on Physiochemical Processes in Solutions and Heterogeneous Systems: Applications in Analytical Chemistry," (2000) J. Analyt. Chem. 55, 1113-1122.

Laszlo, T.S., "Industrial Applications of Microwaves," (1980) The Physics Teacher, Nov. 570-579.

Leitzel, K., Lieu, B., Curley, E., Smith, J., Chinchilli, V., Rychlik, W., & Lipton, A. (1998), "Detection of Cancer Cells in Peripheral Blood of Breast Cancer Patients Using Reverse Transcription-Polymerase Chain Reaction for Epidermal Growth Factor Receptor," Clin. Cancer Res. 4, 3037-3043.

Lennon, G.G., "High-Throughput Gene Expression Analysis for Drug Discovery," (2000) Drug Discov. Today 5, 59-66.

Leonhardt, A. & Mosbach, K., "Enzyme-Mimicking Polymers Exhibiting Specific Substrate Binding and Catalytic Functions," (1987) Reactive Polymers 6, 285.

Lew, A. et al., "Increasing Rates of Reaction: Microwave-Assisted Organic Synthesis for Combinatorial Chemistry," (2002) J. Comb. Chem. 4, 95-105.

Lidstrom, P. et al., "Enhancement of Combinatorial Chemistry by Microwave-Assisted Organic Synthesis," (2002) Combinatorial Chem. High Throughput Screening 5, 441-458.

Lidstrom, P. et al., "Microwave-Assisted Organic Synthesis—A Review," (2001) Tetrahedron 57, 9225-9283.

MacBeath, G. et al., "Printing Small Molecules as Microarrays and Detecting Protein—Ligand Interactions en Masse," (1999) J. Amer. Chem. Soc. 121, 7967-7968.

Makote, R. & Collinson, M.M., "Dopamine Recognition in Templated Silicate Films," (1998) Chem. Commun. 3, 425.

Marx, J., "DNA Arrays Reveal Cancer in its Many Forms," (2000) Science 289, 1670-1672.

Mathew-Krotz, J. & Shea, K. J., "Imprinted Polymer Membranes for the Selective Transport of Targeted Neutral Molecules," (1995) J. Am. Chem. Soc. 118, 8134.

Maugh, T. H., "Semisynthetic Enzymes are New Catalysts," (1984) Science 222, 151-153.

Maugh, T.H. (1983), "Catalysts that Break Nature's Monopoly," Science 221, 351-354.

Maugh, T.H. (1983), "Need a Catalyst? Design an Enzyme," Science 223, 269-271.

Mingos, D.M.P. et al, "Applications of Microwave Dielectric Heating Effects to Synthetic Problems in Chemistry," (1991) Chem. Soc. Rev. 20, 1-47.

Mokaya, R. (1999), "Ultrastable Mesoporous Aluminosilicates by Grafting Routes," Angew. Chem. Int. Ed. 38, 2930.

Nesatyy, V.J. et al. "Microwave-Assisted Protein Staining: Mass Spectrometry Compatible Methods for Rapid Protein Visualisation," (2002) Rapid Commun. Mass Spectrom. 16, 272-280.

Norrlow, O. et al., "Acrylic Polymer Preparations Containing Recognition Sites Obtained by Imprinting With Substrates," (1984) J. Chromatog. 299, 29-41.

Olmedo, L. et al., "Microwave Absorbing Materials Based on Conducting Polymers," (1993) Adv. Mater. 5, 373.

O'Shannessy et al. (1989a), "Molecular Imprinting of Amino Acid Derivatives at Low Temperature (0° C) Using Photolytic Homolysis of Azobisnitriles," Anal. Biochem. 177, 144.

O'Shannessy et al. (1989b), "Recent Advances in the Preparation and Use of Molecularly Imprinted Polymers for Enantiomeric Resolution of amino Acid Derivatives," J. Chromatogr. (1989b) 470, 391.

Pasinetti, G.M., Use of cDNA Microarray in the Search for Molecular Markers in the Onset of Alzheimer's Disease Dementia, (2001) J. Neurosci. Res. 65, 471-476.

Robinson, J.K., "New Molecular Beacon Technology," (2000) American Laboratory, Dec., 28-34.

Roda, A., Pasini, P., Gaurdigli, M., Baraldini, M., Musiani, M., & Mirasoli, M., "Bio- and Chemiluminescence in Bioanalysis," (2000) Fresenius J. Anal. Chem. 366, 752,-9.

Roussy, G. et al., "Foundations and Industrial Applications of Microwave and Radio Frequency Fields," (1995) John Wiley & Sons, NY, pp. 445-466.

Rouhi, A.M., "Boxed in: Chemistry in Confined Spaces," Chem. Engineer. News Aug. 27, 2001, pp. 40-47.

Schena, M. et al., "Quantitative Monitoring of Gene Expression Patterns with a Complementary DNA Microarray," (1995) Science 270, 467-470.

Schmalzing, D. et al., "Capillary Electrophoresis-Based Immunoassays," (2000) Electrophoresis 21, 3919-3930.

Seiden, M. et al., "PCR- and RE-PCR-Based Methods of Tumor Detection: Potential Applications and Clinical Implications," (1996) Important Advances Oncol. Lippincott-Raven, Philadelphia, PA, pp. 191-204.

Shi, H. et al., "Template-Imprinted Nanostructured Surfaces for Protein Recognition," (1999) Nature 398, 593-597.

Sidransky, D., "Nucleic Acid-Based Methods for the Detection of Cancer," (1997) Science 278, 1054-1058.

Slyadnev, M. et al., "Photothermal Temperature Control of a Chemical Reaction on a Microchip Using a n Infrared Diode Laser," (2001) Anal. Chem. 73, 4037-4044.

Stein, D.F. et al., "Microiwave Processing of Materials," Committee on Microwave Processing of Materials, National Materials Advisory Board, Commission on Engineering and Technical Systems, and National Research Council (1994) Microwave Processing of Materials. Washington, DC, National Academy Press.

Varma, R., "Microwave Accelerated Solvent-Free Chemical Reactions," (2001) AMPERE Newsletter, Issue 29, ISSN 1361-8598.

Wathey, B. et al. "The Impact of Microwave-Assisted Organic Chemistry on Drug Discovery," (2002) Drug Discov. Today 7, 373-380.

Wood, W.G., Luminescence Immunoassays: Problems and Possibilities, (1984) J. Clin. Chem. Clin. Biochem. 22, 905-918.

www.novacap.com, Novacap Technical Bulletin (undated).

Yang, P. et al., "Hierarchically Ordered Oxides," (1998) Science 282, 2244.

Yu, H.-M. et al., "Enhanced Coupling Efficiency in Solid-Phase Peptide Synthesis by Microwave Irradiation," (1992) 57, 4781-4784.

Zlotorzynski, A., The Application of Microwave Radiation to Analytical and Environmental Chemistry, Crit. Rev. Anal. Chem. (1995) 25, 43.

Zubritsky, E., "Spotting a Microarray System," (2001) Modern Drug Discov., May issue, 59-71.

Office Communication corresponding to the European Patent Application No. 01979344.7-2404 dated Feb. 15, 2007.

Jansen et al, "Preparation of Coatings of Molecular Sieve Crystals for Catalysis and Separation, " Studies in Surface Science and Catalysis, Elsevier Science B.V., Amsterdam, NI, vol. 85, pp. 215-250 (1994).

Bekkum et al., "Supported Zeolite Systems and Applications, " Studies in Surface Science and Catalysis, Elsevier Science B.V., Amsterdam, NI, vol. 85, pp. 509-542 (1994).

Cornelis & Laszio, "Oxidation of Alcohols by Clay-Supported Iron (III) Nitrate: A New Efficient Oxidizing Agent, " SYNTHESIS, vol. 1980, pp. 849-850 (Oct. 1980).

* cited by examiner

1. Dielectric Surface
2. Surface-bound reactants 1. reagent capture membrane (upper layer)
2. dielectric layer (middle layer)
3. underlying inert support (optional lower layer)

1. reagent capture membrane
2. underlying support (optional)
3. dielectric platform (instrument component)

Top Row (shaded): EQKLISEEDL (SEQ ID NO:1)
Bottom Row (unshaded): EQKHISEEDL (SEQ ID NO:2)

DIRECTED MICROWAVE CHEMISTRY

CROSS-REFERENCE TO RELATED APPLICATIONS

This application is a continuation-in-part of U.S. Patent Application Ser. No. 60/237,192 (filed on Oct. 3, 2000, now abandoned) and Ser. No. 09/968,517 (filed on Oct. 2, 2001), both applications herein incorporated by reference in their entirety.

FIELD OF THE INVENTION

The present invention relates to the field of microwave chemistry. It also relates to the field of biotechnology, specifically microplate- and array chip-based preparative and analytical chemistry.

BACKGROUND OF THE INVENTION

Until now, no one has performed chemical preparations as disclosed herein. Devices are used that emit radiofrequency/microwave energy. The energy is directed to a target object, for example, a microarray chip or a microtiter plate, that contains one or more material(s) that absorb(s) microwave energy. The microwave-generated heat energy accelerates a desired chemical reaction on the surface of the targeted object.

Microwave Chemistry

Microwaves (including radiofrequency or RF electromagnetic radiation) are commonly used in wireless communication devices. Advances in microwave transmission have improved along with tremendous recent technological improvements in the satellite and communications industry (for example, in cell phones and wireless internet).

Microwaves are also well known in common kitchen appliances. Microwave ovens heat water-containing food rapidly because water is efficient at converting microwave energy to thermal energy. Kitchen microwave ovens emit microwaves at a frequency of 2.45 GHz, which is well within the microwave absorption spectrum of water. Frequencies outside of the absorption spectrum of water would not heat food as well.

Another use for microwaves is in chemical reaction applications (Bose et al., 1997; Bradley, 2001; Wathey et al., 2002; Lew et al., 2002). Microwave chemistry refers to the use of microwaves to accelerate chemical reactions. Reactions are usually carried out using microwave radiation to heat bulk solutions that contain the reactants (Mingos & Baghurst, 1991; Zlotorzynski, 1995). Often these reactions are carried out in non-aqueous solvents. Microwave ovens specifically designed for use in carrying out microwave chemistry of bulk reaction solutions are commercially available (CEM Corporation (Mathews, N.C.), Milestone, Inc. (Monroe, Conn.), Personal Chemistry AB (Uppsala, Sweden), PerkinElmer Instruments (Shelton, Conn.)).

Microwave accelerated reactions are sometimes run on solvent-free supports such as alumina and silica (Varma, 2001; Bose, 1997; Bram et al., 1990). The supports can be doped with reagents, for example in detoxifying waste. The supports are chosen because they are inexpensive and recyclable agents which non-specifically adsorb/extract the reagent of interest. No specific binding of (such as by antibodies) is used to capture reagents.

Microwave-enhanced catalysis has also been described (Roussy & Pearce, 1995). The term "microwave-enhanced catalysis" has been used to refer to conventional catalysis, rather than to catalysis that occurs in enzyme-like binding pockets in aqueous solution. One example of such usage of the term "microwave-enhanced catalysis" is the isomerization of liquid hexane using a metallic $Pt/Al_2O_3$ catalyst. Another example is the partial oxidation of gaseous methane using a catalyst that is an oxide of $SmLiO_2$ doped with CaO and MgO (Roussy & Pearce, 1995).

Another example of the application of microwaves to accelerate chemical reactions is the use of microwave-absorbing particles to enhance the heating of a bulk solution (Holzwarth et al., 1998). In this case, dispersed cobalt and magnetite nanoparticles were used as microwave (2.45 GHz) absorbers to heat a bulk xylene solution. Xylene is a non-polar solvent not appreciably heated by microwaves at 2.45 GHz. In one such case, microwaves were used to accelerate the rate of an enzyme-catalyzed reaction (Kidwai et al., 1998). In another case, Milestone, Inc. (Monroe, Conn.) sells microwave-absorbing/heating composites of PTFE and graphite which are designed to be dropped into test tubes to accelerate microwave heating of solutions during chemical syntheses. However, in these cases the microwaves are not directed to heat a surface, but used to heat the bulk solution.

In another application, microwaves have been used to heat the bulk solvent during solid-phase combinatorial chemistry (Kappe, 2001; Bradley, 2001; Lidstrom et al., 2001). In these cases, conventional resins (polystyrene, for example) function as solid scaffolds for chemistry. The bulk solution was the target of the microwave heating.

In another case, microwaves were used to accelerate a chromogenic reaction between noble metals and chromogenic reagents. This analytical reaction was performed in solution by flow injection analysis (FIA) (Jin et al., 1999). The reaction depended on bulk solvent heating rather than targeted dielectric material heating.

In yet another case, microwaves were used to enhance the solution phase formation of a fluorescent complex of aluminum (Kubrakova, 2000). The fluorescence intensity could be used to measure aluminum ions in solution. Again, the reaction depended on bulk heating of solvent.

In yet other cases, microwave heating has been used in biochemistry applications. In one instance, microwave heating-assisted protein staining (Nesatyy et al., 2002). In another instance (Boon & Kok, 1989), microwave heating was used to accelerate enzyme-linked immunosorbent assays (ELISAs). In none of these was microwave heating directed to a solid surface, but rather microwave heating was applied to heat a bulk aqueous target.

Natural and Man-Made Enzymes

Nature uses specifically folded proteins called enzymes to catalyze specific reactions necessary for the function of a living organism. Nature also uses non-catalytic proteins, such as receptors and antibodies to affect other biological processes. Both catalytic and non-catalytic proteins have remarkable pockets on their surfaces that bind to the appropriate molecule with exquisite specificity. In the case of enzymes, when the appropriate molecule is bound in the binding pocket (called an "active site"), a chemical reaction takes place that converts the molecule (substrate) into a chemically different molecule (product). The reaction product dissociates from the active site, allowing the (unaltered) enzyme to bind and catalyze another reaction "turnover".

Protein-based enzymes, receptors, and antibodies are often used in industry, medicine, and diagnostics as reagents. For example, antibodies are used as therapeutic agents for various diseases including cancer and rheumatoid arthritis. Enzymes are used to "fade" denim blue jeans and to process high fructose corn syrup. Antibodies and enzymes are used in immunoassays in medical diagnostics. Despite the widespread use of naturally occurring antibodies and enzymes, many laboratories have sought to create artificial antibodies, receptors, and enzymes. One drawback of the use of natural proteins, or modified natural proteins, for practical purposes, is that proteins are not particularly stable molecules. Artificial reagents would have greater stability to non-physiological temperatures, pH values, non-aqueous solvents, and salt concentrations. Also, natural proteins are susceptible to degradation by contaminating enzymes called proteases that hydrolytically cleave and inactivate other proteins. In addition, even under ideal storage conditions (cold storage in a suitable buffer) the shelf life of proteins can be very short. Finally, in many cases a binding or catalytic reagent is desired for which there is no known natural antibody or enzyme. For example, an antibody may be desired that binds a very small molecule such as methanol or an enzyme may be desired that carries out a chosen stereospecific reaction during preparation of a fine chemical.

Because of the above-stated drawbacks of natural proteins, many laboratories have developed non-protein biomimetic compounds that function in the same way as antibodies or enzymes. A wide range of classes of chemical structures has been shown to be useful as artificial proteins. In all cases, the artificial biomolecules have binding pockets that specifically bind to a molecule of choice. These include, but are not limited to; molecularly imprinted polymers (Dai, et al., 1999; Dickert & Thierer, 1996; Leonhardt & Mosbach, 1987), chiral ligands (Maugh 1983a), cavitands (Maugh 1983b, Breslow et al., 1983) and zeolites, and other low molecular weight organic synthetic receptors (Borchart & Clark, 1994). In addition, natural proteins are often sought out or modified to have enhanced stability (thermal or other)(Maugh, 1984).

Individuals who have made artificial enzymes or antibodies/receptors have never reported the possibility that directed microwave energy could be used to promote the rate of a biospecific chemical reaction.

The present invention combines salient features of these two previously unassociated fields. By combining certain aspects of these fields it has been discovered that the rate of chemical reactions can be accelerated by the energy of microwave radiation and with the exquisite regio- and stereo-specificity of natural enzymes.

The present invention reveals a novel means of using microwave energy to specifically accelerate chosen chemical reactions. The reaction specificity comes from the fact that the microwaves are directed to lossy (see definitions below) materials that contain specific binding sites for the desired reactant. The invention describes new uses of microwave radiation. It has never before been disclosed how to direct dielectric heat to accelerate the reaction of a specific molecule in a mixture of similar and/or dissimilar molecules. In this way, the invention describes a new form of artificial enzyme. The results are obtained by using a dielectric material that has substantially better heating properties than water at the chosen microwave emission frequency. A specific reactant-binding molecule is in association with the preferentially heated dielectric material, causing the enhanced reaction of bound reactant.

The present invention also discloses how microwaves can further be used to prepare the surface in advance of such reactions. As described above, natural and artificial enzymes require a specific binding interaction between at least two chemical moieties and an energetic impetus for a reaction to occur (microwave energy in this case). Microwave-facilitated surface preparation includes but is not limited to accelerating the binding of a biomolecule such as a protein or DNA to the surface or accelerating the synthesis of a peptide or other ligand or substrate.

OBJECTS OF THE INVENTION

The invention is directed toward an improved process and apparatus for accelerating the rate of specific chemical reactions. A further objective of the invention is to confer tailored enzyme-like regio- and stereo-specificity to a reaction. A still further objective of the invention is to provide such improved reaction rates and specificity to a diverse number and type of chemical reactions. It is yet another objective of the invention that the accelerated reactions be controllable, so that they can be selectively turned on or off, or be modulated, by a user at will. It is yet another objective of this invention to allow specific reactions to be accelerated regardless of whether the reaction is in a homogeneous or heterogeneous solution or suspension, or is bound or otherwise associated with a solid support (such as a surface, bead, etc.). It is yet another objective of the invention to provide a method for accelerating a chosen reaction in the presence of other compounds that may be very similar in structure to the desired reactant, but will not appreciably react. It is yet a further objective of the invention to use microwaves to accelerate a chemical reaction to prepare a surface for a subsequent bioanalytical reaction. It is yet another objective of this invention to use the piezoelectric properties of a microwave-targeted material to accelerate biomolecular binding interactions. It is yet another objective of this invention to direct microwave heating to the surfaces of bioanalytical array chips and microtiter plates to accelerate preparative and analytical reactions. It is yet another objective of this patent to render harmful biomolecules or bioorganisms inactive using microwave heat following a bioanalytical test.

SUMMARY OF THE INVENTION

Figure 1:
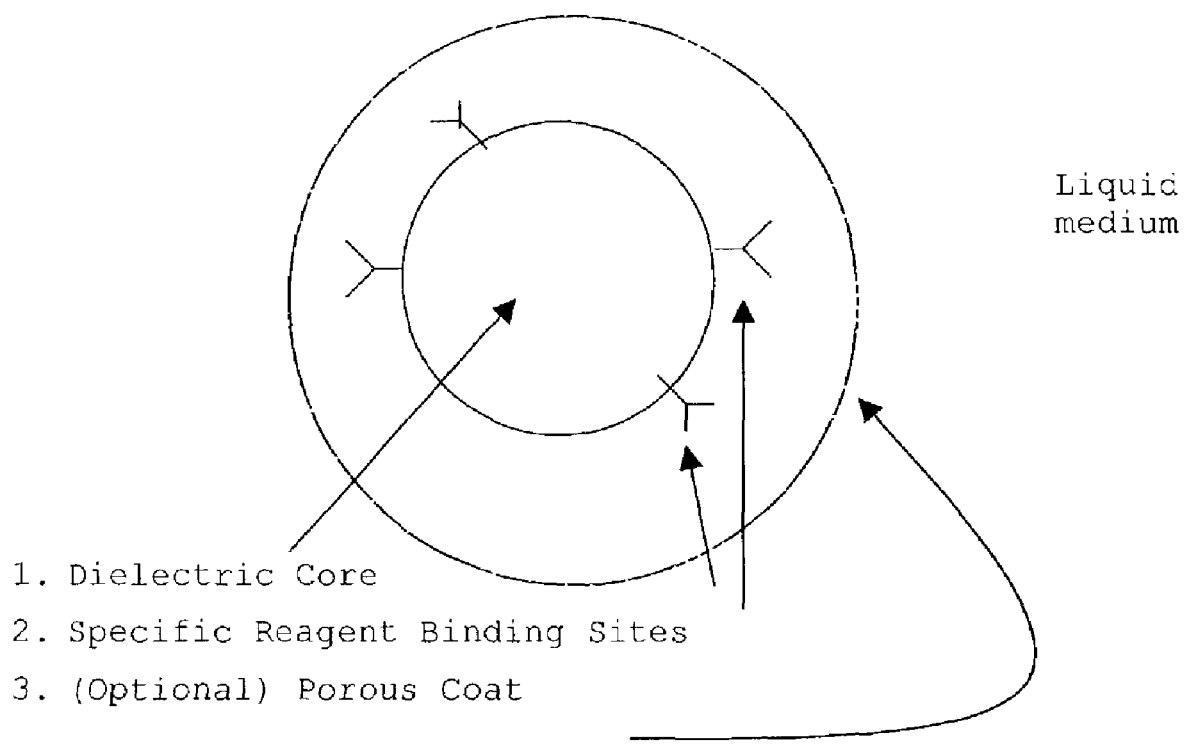
FIG. 1: Directed microwave chemistry. The two most important features are: (1) a dielectric object that absorbs microwaves, and is in contact with or in close proximity to (2) a binding surface that captures the reactant of choice. In essence, heat is targeted to the reactants by the microwave-absorbing dielectric. Microwave irradiation thereby triggers a specific reaction to take place at or near the surface of the dielectric.

The invention describes a means in which chemical reactions (catalytic or stoichiometric) can be accelerated and be given exquisite enzyme-like specificity. The reactions preferably occur on solid phases or surfaces (hereinafter collectively referred to as "solid supports"). Suitable solid supports preferably contain: a dielectric (microwave absorbing) material and a reactant surface on which one or more biological molecules are covalently or non-covalently attached. The solid support can be in many forms, most notably beads and planar or curved surfaces. Frequently the solid supports are microchip surfaces or the wells of microtiter plates used for bioanalytical reactions. Alternatively, the solid support could be in the form of test tubes, centrifuge tubes, or Petri dishes. The solid supports may be bathed in aqueous or organic solution containing the chosen reagent. Next, depending on the application, the solid supports are preferably either left in the solvent or are removed, for example, into air, etc. Microwaves are then emitted into the solid surface. In cases where the solid support is left in solvent, the microwaves are emitted at a frequency that heats the dielectric more than the solvent. The instrument power, frequency, and duration of the microwave emission are pre-determined in the laboratory. Following microwave heating, a change in the reagent may be noted by some physicochemical change that takes place in the formation of product(s) from reactant(s). The specific chemical rate acceleration can be used for preparative and/or analytical applications. In analytical applications, the reaction may optionally be monitored and/or quantitated, for example in medical diagnostics, by an accompanied observable physico-chemical change (color change, for example). In preparative applications, the presence of a microwave-dielectric layer can assist in surface chemistry to prepare the solid support for subsequent analytical reactions. There are two preferred ways in which the dielectric layer can be used preparatively. One such preferred way is that microwave heating of the surface can accelerate chemistry by a thermal effect—for example, by accelerating antibody or nucleic acid binding to that surface, or by accelerating the chemical synthesis of small molecules such as peptides on the surface. The second preferred way is by accelerated binding of protein or nucleic acid by a piezoelectric effect. Many dielectrics such as ceramics are known to have piezoelectric properties. Passage of an electric current through the dielectric causes ultrasonic vibrations in the dielectric and accelerated biomolecular binding.

In accordance with the principles of the present invention, the reaction on a solid support may be accelerated by: (1) adjusting the concentration of the reactant by binding to a large number of specific binding sites on the solid support, or (2) adjusting the temperature difference between the dielectric/artificial enzyme and the bulk solution.

In detail, the invention provides a method for accelerating a chemical reaction involving a reactant, the method comprising;

(a) contacting a composite with the reactant, the composite comprising a solid material susceptible to dielectric heating, (b) applying an electromagnetic field to the composite, the electromagnetic field being sufficient to result in dielectric heating of the solid material, and (c) allowing the composite being heating to react with the reactant, whereby the resultant product is contained in the composite, thereby accelerating the chemical reaction.

The invention particularly concerns the embodiment of such method further comprising the step of measuring the extent or rate of the chemical reaction. The invention additionally concerns the embodiments of such methods that further comprise the steps of;

(d) contacting the composite with one or more additional reactant(s), (e) allowing the additional reactant(s) to react in one or more biospecific interactions, and (f) measuring the extent or rate of one or more of the biospecific interactions.

The invention additionally concerns the embodiments of such methods that further comprise the steps of;

(d) contacting the composite with one or more additional reactant(s) for one or more further reactions, (e) applying an electromagnetic field to the composite, the electromagnetic field being sufficient to result in dielectric heating of the solid material, the additional reactant(s) being heated by heat transfer from the heated solid material, (f) allowing the heated additional reactant(s) to react, thereby accelerating one or more of the further reactions, and (g) measuring the extent or rate of one or more of the further reactions.

The invention additionally concerns the embodiments of such methods that further comprise the steps of;

(d) measuring the extent or rate of the reaction, (e) contacting the composite with one or more additional reactant(s), (f) applying an electromagnetic field to the composite, the electromagnetic field being sufficient to result in dielectric heating of the solid material, the additional reactant(s) being heated by heat transfer from the heated solid material, (g) allowing one or more of the heated second reactant(s) to react, thereby accelerating one or more of the further reactions, and (h) measuring the extent or rate of one or more of the further reactions.

The invention additionally concerns the embodiments of such methods, wherein the reactant is selected from the group consisting of an amino acid, a protein, a peptide, an oligonucleotide, and a polynucleotide.

The invention additionally concerns the embodiments of such methods wherein the reaction is a noncovalent adsorption reaction, and/or wherein the reactant is an amino acid, and/or wherein the reaction is a covalent conjugation reaction.

The invention additionally concerns the embodiments of such methods wherein the wavelength of the applied field is between 1 cm and 100 m.

The invention additionally concerns the embodiments of such methods wherein one or more of the chemical reactions is selected from the group consisting of: a chemiluminescent reaction, a reaction resulting in a change in visible or ultraviolet color, and a reaction involving a change in fluorescent properties. The invention additionally concerns the embodiments of such methods wherein one or more of the reactant(s) is a product of an enzymatic reaction.

The invention additionally concerns the embodiments of such methods wherein the wavelength of the applied field is between 1 cm and 100 m.

The invention additionally concerns a composite comprising the composite obtained by the above methods.

The invention additionally concerns the embodiments of such a composite that comprises a solid material responsive to dielectric heating bearing a surface molecule capable of biospecific interaction with a reactant molecule.

The invention additionally concerns the embodiments of such a composite wherein the surface molecule is bound or immobilized to the surface via a noncovalent adsorption reaction.

The invention additionally concerns the embodiments of such a composite wherein the surface is capable of a covalent conjugation reaction with the reactant molecule and/or wherein the surface is selected from the group consisting of a microarray chip, a macroarray chip, a test tube, a Petri dish, and a microtiter plate. The invention additionally concerns the embodiments of such a composite wherein the solid material has piezoelectric properties.

The invention additionally concerns a method for accelerating a chemical reaction of a reactant, the method comprising;

(a) contacting a composite with one or more reactants, the composite comprising a solid material susceptible to piezoelectric sonication and dielectric heating, (b) applying an electric current to the composite, the electric current being sufficient to result in piezoelectric vibration of the solid material, and (c) allowing the reactant to react with the composite, thereby accelerating the chemical reaction.

The invention additionally concerns the embodiment of such method that further comprises the steps of;

(d) contacting the composite with one or more additional reactant(s), (e) applying an electromagnetic field to the composite, the electromagnetic field being sufficient to result in dielectric heating of the solid material, the additional reactant(s) being heated by heat transfer from the heated solid material, (f) allowing the heated second reactant to react, thereby accelerating the second reaction, and (g) measuring the extent of the second reaction.

The invention additionally concerns the embodiment of such method wherein the composite contains a ceramic material.

DEFINITIONS

Accelerate: To increase the rate of a chemical reaction, preferably by at least 10%, more preferably by at least 50%, and most preferably by at least 100% or more.

Aqueous Solution: A liquid medium that is more than 50% water by volume.

Artificial Antibody (or Receptor): A synthetically produced molecule that contains a binding pocket designed to be complementary in shape and/or charge to a molecule which it binds. It may be made of a single molecule, such as a small organic molecule or a man-made polymer, or it may be a bulk substance such as an acrylic polymer particle or a surface of silica. The artificial biomolecule specifically binds to the complementary molecule.

Artificial Enzyme: A synthetically produced molecule that has one or more binding sites that are complementary in shape or charge to another molecule. The artificial enzyme binds to the complementary molecule and causes the bound molecule to undergo a chemical transformation.

Biospecific Interaction: The contact of a biological molecule to a biological or non-biological molecule via three or more spatially distinct physical interactions. The interactions are typically van der Waals interactions, hydrogen bonds, and ionic interactions. Biospecific interactions may also involve covalent bonds.

Chemical Reaction: The chemical transformation of one or more molecules (reactant(s)) to form one or more molecules (product(s)). The definition includes covalent (such as hydrolysis) and noncovalent (such as binding events) transformations.

Chip: An essentially planar object that has one or more zones on its surface for desired chemical reactions to take place. A chip is preferably small enough and light enough to be held in one hand. If biological molecules are involved in the reactions, the chip is also known as a biochip.

Composite: A solid made of two or more distinct types of materials or molecules. If a composite is made of multiple materials, the materials may be blended or physically distinct. If physically distinct, the materials may be irreversibly joined (e.g., glued together) or reversibly joined (e.g., snapped together).

Dielectric Heating: Heating of a dielectric (electrically-insulating) material by electromagnetic radiation in the wavelengths between approximately 5 cm and 100 m.

Lossy Material: A (dielectric) material that loses absorbed microwave energy in the form of heat.

Macroarray: A panel of a plurality of reaction zones on a chip ranging from 1 to 1000 zones.

MATTR: "Microwave-Accelerated Targeted Triggered Reaction" technology.

Microarray: A panel of reaction zones on a chip numbering greater than 1000.

Microtiter plate: An object commonly used in biomedical laboratories containing multiple reaction wells. Typically, microtiter plates are disposable, made of clear acrylic, and have 24 (arranged in a 4×6 array), 96 (8×12), 384 (16×24), or 1536 (32×48) wells.

Microwave: Electromagnetic radiation in the range of $3 \times 10^2$ to $3 \times 10^4$ MHz (wavelengths of 1 m to 1 cm). Dielectric heating occurs in this range, but also occurs at longer (radio) wavelengths (up to 100 m), which could be alternatively used. Overall, microwave heating (herein defined to include radiofrequency dielectric heating) frequencies span wavelengths of about 1 cm to 100 m.

Microwave Oven: A device that emits microwave radiation at a pre-determined wavelength into an internal chamber. The chamber is closed to limit the escape of microwaves.

Molecular Imprinting: A process whereby specific binding sites to a chosen target (imprint) molecule are introduced into synthetic materials. The binding material is usually an organic polymer. Typically, functional and cross-linking monomers are co-polymerized in the presence of the imprint molecule, which acts as a molecular template. Subsequent removal of the template molecule reveals binding sites that are complementary in shape and size to the imprint molecule. In this way, molecular memory is introduced into the polymer, enabling it to re-bind the imprint molecule with high specificity.

Organic Solution: A liquid medium that is more than 50% organic solvent by volume.

Oligonucleotide: A nucleic acid molecule having 50 or fewer nucleotide residues.

Piezoelectric Materials: Substances which, when mechanically deformed, generate an electric charge. Conversely, when an external electric field is applied to piezoelectric materials they mechanically deform (change their physical dimensions). Collectively these are called piezoelectric effects.

Polynucleotide: A nucleic acid molecule having more than 50 nucleotide residues.

Porous: A solid material containing channels through which water and other liquid molecules can pass.

Thermal Proximity: The situation in which one substance is close enough to a second substance to permit substantial heat transfer to occur between them. In preferred embodiments, the first and second substances are bathed in an aqueous or organic liquid solution. In many instances, the bulk of the second substance is not in thermal proximity with the first substance and thus does not receive substantial heat transfer to or from the first.

Thermocouple: A sensor for measuring temperature consisting of two dissimilar metals, joined together at one end. The metals produce a small unique voltage at a given temperature. The voltage is measured and interpreted by a thermocouple thermometer.

Waveguide: A structure that causes a wave to propagate in a chosen direction. It is accomplished by an intimate connection between the waves and the currents and charges on the boundaries, or by some condition of reflection at the boundary.

Zeolite: Porous inorganic solids used in catalyzing chemical reactions. Zeolites are rigid structures based on regularly repeating patterns of aluminate and silicate tetrahedral linked by oxygen atoms.

DETAILED DESCRIPTION OF THE PREFERRED EMBODIMENTS

Microwave Heating

Until recently in the history of mankind, conventional bulk heating (fire, etc.) was the only method of causing temperature increases (and acceleration of chemical reactions). In the past half century, a new fundamentally distinct form of heating has been developed called microwave heating (herein defined to include dielectric heating—see definitions). In microwave heating, electromagnetic radiation is applied to a sample. Compounds within the sample that are dielectrics that absorb microwaves of the applied frequency undergo increases in temperature. Dielectric materials have unique spectral characteristics of frequency versus heating ability, with different substances heating more effectively at different frequencies (Gabriel et al., 1998). The most important aspect is that in contrast to conventional heating, where the heat is applied from the outside and moves inward, in dielectric heating, the heating is directed to materials with characteristically appropriate dielectric properties. Although dielectric heating is referred to here as microwave heating, dielectric heating can also occur at radio frequencies. This invention is intended to include those effects.

According to the Arrhenius equation, the rate of a reaction can accelerate due to a decrease in the activation energy (i.e., a change in the reaction mechanism, as with enzymes) or from an increase in the pre-exponential factor, which reflects the frequency and efficiency of collisions between reacting particles. The second reason is closely related to the mechanism of action of microwaves on substances and is a major reason for a considerable acceleration of chemical processes in a microwave field (Kubrakova, 2000)

Dielectric heating depends on a number of factors including the frequency of the microwave irradiation and the absorption properties of the dielectric at that frequency. All dielectric materials have characteristic absorption spectra (frequency vs. heating ability). For example, in a conventional kitchen microwave oven, the microwave frequency (2.45 GHz) is very good for heating water, but not good for heating other materials (for example, a cup that holds the water). If the frequency of the microwave emission would be changed, in theory one could heat the cup but not the water (depending on the relative dielectric absorption characteristics of water and the cup). Thus, it is possible to heat materials in water without heating the water using dielectric heating. Of course, once the material is heated, heat will transfer into adjacent water unless the heated material is covered with a heat-insulating layer.

The dielectric is chosen (initially by literature or screening of compounds), covered by binding molecules (for example by covalent attachment, adsorption, entrapment (inside the macroporous or mesoporous insulating layer), etc., this layer may be coated with a porous layer. The dielectric is added to an aqueous or organic solution of reactant. Microwave irradiation occurs, and the appropriate product is formed.

Physical Components of a Preferred Embodiment of the Invention:

The physical components of a preferred embodiment of the invention are:

1) The microwave/radio frequency source. The reactions may be carried out within a cavity of a microwave generator, or within a waveguide. Microwaves can be generated by various devices including a magnetron, a solid-state device (such as a Bluetooth or Wi-Fi (IEEE 811.b)), a klystrom, a cross-field amplifier, a traveling wave tube, a backward-wave oscillator, or any combination thereof. The microwave emission is in the frequency range of 300 to 30,000 MHz (wavelengths of 1 m to 1 cm). Dielectric heating also occurs at lower (radio) frequencies of down to 3 MHz (wavelengths of up to 100 m), which can be alternatively used. Overall, microwave/ dielectric heating frequencies span wavelengths of about 1 cm to 100 m. Electromagnetic heating throughout this range is considered part of this invention. The frequency used would depend on factors including the identity of the dielectric material to be heated.

Attractive frequencies for this invention include 0.915 GHz, 2.45 GHz, 5.85 GHz, and 22.125 GHz. The U.S. Government currently approves these frequencies for use for industrial, scientific, and medical uses (Boon & Kok, 1989). Other frequencies may also be attractive provided that the emission within the microwave chamber is sufficiently shielded (to prevent interference with communications uses of microwaves). "Frequency-tunable" microwave ovens can be made and used for this invention (Microwave Research Center, Eagan, Minn.; Microwave Research & Applications, Inc., Laurel, Md.). Most commercially available microwaves, including home kitchen microwaves emit at 2.450 GHz, although other frequencies are commercially available. For example, Microdry, Inc. (Crestwood, Ky.) and Cober Electronics (Norwalk, Conn.) sell 0.915 GHz microwaves. Of the above-listed frequencies, 2.45 GHz is attractive because it is a widely accepted frequency used in numerous existing devices such as domestic microwave ovens and many wireless communications devices (Wi-Fi and Bluetooth). Because of widespread use of these devices, design and manufacturing know-how of 2.45 GHz emitters including magnetrons and solid-state devices are well known. A frequency of 0.915 GHz is also an attractive frequency for aqueous applications because water is least susceptible to dielectric heating at this frequency (Laslo, 1980). Table 1 shows the frequency dependence in microwave heating of water.

TABLE 1

| Relative Loss Factors for distilled $H_2O$ (Susceptibility to Microwave Heating) | | |
|---|---|---|
| 0.915 GHz | 2.450 GHz | 5.800 GHz |
| 1.4 | 11.3 | 4.3 |

It is envisioned that the reactions may be carried out with the dielectric/binding composite submerged in a liquid- or solid-phase reaction mixture inside a microwave-generating device. By applying microwave heating to the dielectric in the reaction mixture, multiple turnovers (catalysis) will be possible at the liquid/solid interface.

Microwaves generated will strike the heated dielectric solid phase (microchip, microtiter plate, flexible film, etc.) either in a cavity, such as a microwave oven chamber, or in a waveguide. Generally, when microwaves are generated (by for example a magnetron) in a microwave oven, they are directed by a waveguide into a cavity where the sample that is to be heated is placed. There are advantages to placing a sample in a waveguide rather than an oven cavity. Microwaves are uniform in a waveguide, but become less uniform in an oven cavity, where standing waves often create "hotspots".

Central to a preferred embodiment of this invention is that microwaves strike and heat the dielectric that is in contact with the reaction surface. The microwaves may bathe the dielectric from multiple directions, from the "reaction side" or from the "dielectric side" (FIG. 2). Thus, it is not a necessity that the reactants themselves are irradiated with microwaves—only that they receive heat from the dielectric material. Indeed, in some cases it may be preferable not to directly irradiate the reaction surface. For example, the reaction surface may contain materials that are not compatible with direct microwave irradiation (for example, a metal thermocouple for measuring temperature).

Reactions run without a bulk solution are useful in analytical applications (for example in medical diagnostics). In diagnostics, the reactant solution might contain a biological fluid from a patient. Following capture of the desired molecule, detection can be facilitated by a microwave-accelerated reaction. For example, microwaves could cause a color change in the analyte. Alternatively, a signaling molecule, such as a labeled anti-analyte antibody can be added. The label on the antibody could undergo a reaction upon microwave irradiation to form a luminescent or fluorescent signal.

Figure 2A:
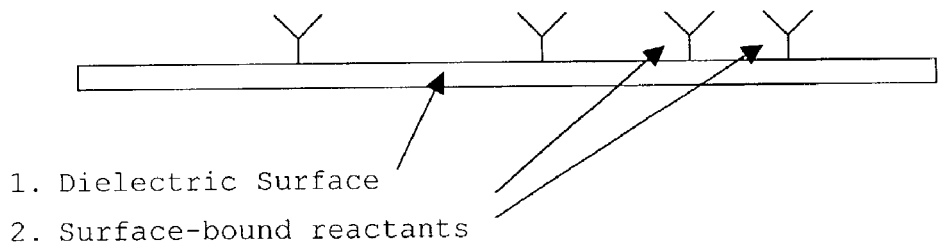
FIGS. 2A-2C: Planar surface-based materials for directed microwave chemistry (e.g., on a microarray chip or in the well of a microtiter plate). The most important features are described in the legend of FIG. 1. The surface on which the reaction occurs may contain the dielectric as shown in FIG. 2A or be adjacent to the dielectric, as shown in FIG. 2B and FIG. 2C. In cases where the dielectric is adjacent to the reaction surface, the dielectric may be a permanently attached component (e.g., part of the microarray chip or microtiter plate) as in FIG. 2B, or the reaction surface (e.g., microarray chip or microtiter plate) may simply be placed onto a dielectric platform during the microwave reaction (e.g., the dielectric could be a permanent component of the microwave-emitting instrument) as in FIG. 2C.
Figure 2B:
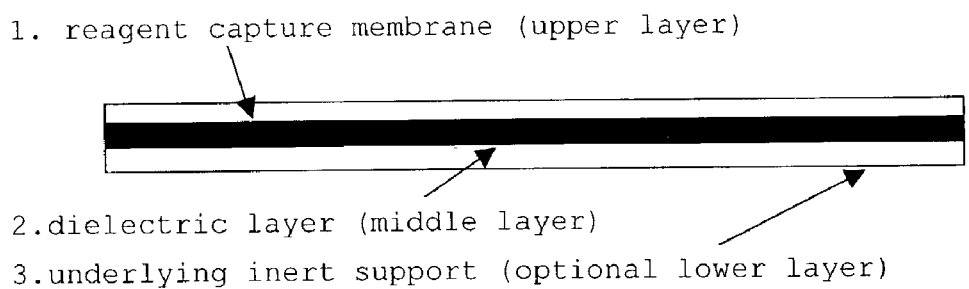
Figure 2C:
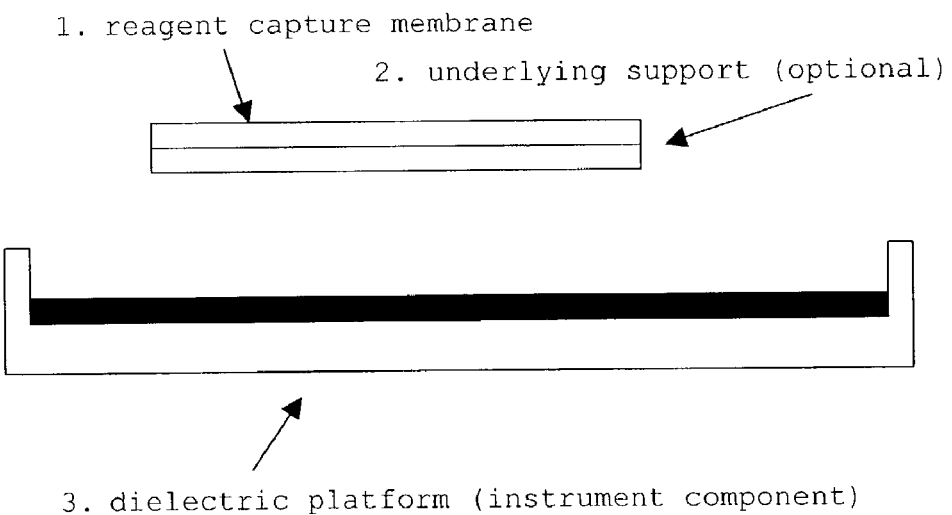

2) The dielectric material. The dielectric material will preferably be a solid support in contact with the liquid reactant solution. The support may have any of a variety of geometries. It may be a planar surface (e.g., a part of a coating or a wall of a chamber or the surface or a chip or cartridge). A suitable planar dielectric may be part of a chip, such as a multi-analyte disposable biological assay chip (protein chip or DNA chip) or part of a microtiter plate. Such apparatus may commonly either possess the dielectric material as one or more spots on their surface, or may comprise a continuous layer. Alternatively, the dielectric material could be in suspension in the form of a particle, such as a bead. Similar use of dielectric material can be used in other types of reaction vessels such as microtiter plates, test tubes, Petri dishes, and centrifuge tubes. The dielectric material can be integrated into the reaction vessel (such as a Teflon (PTFE)/graphite composite, or it can be deposited onto the bottom of the vessel (such as a barium titanate/gelatin glue) or it can be physically separate from the reaction vessel. In the latter case, the dielectric could be part of the microwave instrument (FIG. 2C). For example, a dielectric-containing reaction vessel holder could be permanently affixed to the oven cavity or within the waveguide. The present invention only requires that the dielectric is heated in proximity to bound biological molecules, not that the dielectric is physically a part of the reaction vessel (microchip, microtiter plate, etc.). This particular embodiment is attractive because microwaves could access the dielectric from "below", such that the chip itself is not irradiated, but receives heat by conduction from the underlying dielectric material. The dielectric is built into the wall of a waveguide or microwave oven cavity.

3) The reaction to be carried out. Briefly, the reaction can be any organic or inorganic reaction that is accelerated by heat. Preferably, the reaction will be fairly slow at room temperature under the conditions chosen, but it will be rapid at elevated temperatures. For analytical applications, the reaction will be chosen depending on the detection method (change in color, luminescence, etc.).

4) The surface-bound molecules that specifically interact with reactant molecules. Molecules that specifically bind to the reactant molecule will preferably be attached to the surface of the dielectric material. Such binding molecules can be, for example, antibodies (or derivatives thereof), receptors, receptor ligands, enzymes (or derivatives thereof), peptides, amino acids, nucleic acids, molecularly imprinted polymers, zeolites, cavitands, or any other high or low molecular weight molecule that may specifically bind to the reactant. The binding molecule is preferably thermally proximal to the dielectric material. It can be adsorbed, physically trapped, covalently bound, or otherwise associated with the dielectric material (FIG. 2A). Alternatively, a layer such as a membrane may be cast or placed over the dielectric, so as to be in contact with it. For example, nitrocellulose or nylon membranes can be used to capture DNA (FIG. 2B, FIG. 2C). Capture reagents (antibody or DNA, etc.) are adsorbed to the membrane in spots. A variety of usable membranes are available. Particles bearing capture reagent can be entrapped in the membranes (Jones, 2001). Covalent or noncovalent immobilization of the surface-bound molecules to the surface may be hastened by microwave-directed heating of the proximal dielectric.

5) A detection/monitoring method (for analytical applications of the invention). Physico-chemical changes that accompany the formation of product(s) from reactant(s) are observed. Which detection method is used is not critical to the invention itself (many detection methods will do), but the detection method must be chosen to correspond with the reaction to be carried out (e.g., colorimetric, luminescent). The detector may be built into the instrument or detection may be carried out, post-heating, in another instrument, or by eye. The monitoring method can be a change in color, fluorescence, luminescence, mass, or any other detectable property. The chosen detection method depends on the chosen reaction and the scale of the reaction. Many detection methods are well known.

6) The optional porous thermally insulating layer. Optionally, a porous thermally insulating layer may be provided to contact or surround the dielectric/binding molecule layer. This layer would allow passage of reactant molecules, but would diminish the bulk transfer of heat from the dielectric material to bulk water or other solvent. For example, this insulating layer could be macroporous or mesoporous. In at least one example, molecularly-imprinted polymers, the insulting layer and the binding molecule could be the same. The optional porous layer can be any material that permits the passage of reactants and products and has some thermal insulating properties. Essentially, the purpose of this layer is to slow heat conduction from the dielectric to the bulk aqueous phase. This layer may not be necessary, especially if the amount of dielectric is small compared to the volume of water. Many types of porous materials are polymers.

In general, the porous layer can be any material that allows the reactant(s) to pass through pores in its surface to reach their specific binding sites. The porous layer should be made from a material that has thermal insulating properties, although any ability to slow diffusion of water will be beneficial. Some materials that could be used are organic polymers, which could be crosslinked or formed on the surface or adsorbed and crosslinked dextran, gelatin, or agarose. Others include synthetic polymers such as acrylates, polyacrylamide, silica, and poly(styrene-divinylbenzene).

7) The optional special container. A functional alternative to the optional porous thermal insulating layer is to have an optional special container that holds the reaction solution. The container is "special" in that it cools the solution. The container lining may therefore contain a Peltier cooling device or an ice-water lining, or another means of withdrawing heat from the bulk solution. The effect of such a cooling container is to allow microwave heating to be more selectively directed to the dielectric material, and less toward the bulk solution. Heat transferred from the dielectric to the bulk solution would be transferred to the cooled container lining. Cooling containers are well known in many instruments, such as spectrophotometers used in cryospectroscopic work.

8) Additionally, in some cases it may be desirable to monitor and/or control the temperature of the dielectric. A thermocouple can be used to measure the temperature of the dielectric provided that the dielectric is structurally amenable (for example a chip-based dielectric. One example is if the dielectric is coated on a disposable chip (i.e., a microscope slide). A thermocouple could be used to contact the chip and monitor the temperature during heating. Moreover, thermocouple temperature measurement could be used to control the temperature by controlling the power of the microwave oven. If the dielectric temperature reached a certain level, say 300° C., the microwave could be automatically shut off. When the temperature dropped, to say 290° C., the thermocouple would cause the microwave to begin heating again. Such thermocouple-based temperature control is well known art (Huhmer and Landers, 2000; ASTM, 1993; Kreider, 1989). Alternatively, temperature can be measured using non-contact spectroscopic techniques (Boon & Kok, 1989; Slyanev et al., 2001). Both thermocouples and spectroscopic methods have been used to measure microchip temperatures (Huhmer and Landers, 2000; Slyanev et al. 2001).

Above are described the required and optional components of a preferred embodiment of the invention. The are the main variables associated with these components are: (1) the microwave generating instrument and conditions used (generator type (magnetron, solid-state chip, etc.), frequency, time, power, sample placement (in oven cavity vs. in waveguide)), (2) the material composition of the dielectric, (3) the reaction to be carried out, (4) the molecule that binds to the reactant (more generally-speaking, the assay to be carried out), (4) the detection method (for analytical applications), (5) the format of the reaction vessel (microarray chip, microtiter plate, etc., and whether the dielectric is integrated into the reaction vessel or is a part of the microwave instrument), and (6) the signal detection method. Each of these could be different for different applications. Each variable will be discussed separately:

1) The microwave instrument: The parameter that describes the ability of a dielectric material to convert electromagnetic energy into other forms of energy (heat) is the dissipation factor or loss tangent (Tan$\delta$). For every material, Tan$\delta$ is frequency dependent. Materials that have much higher values of Tan $\delta$ than the chosen solvent (at a given frequency) are attractive for this invention. The frequency can be chosen to optimize the ratio: Tan $\delta_{dielectric}$/Tan $\delta_{solvent}$. Thus, for the invention to reach its fullest potential, the microwave frequency, and the absorbing characteristics of the dielectric (desired high absorbing) and solvent (desired low absorbing) must be optimized. In applications where multiple turnovers (catalysis) are desired, microwave irradiation can be made to occur while the dielectric is bathed in the reactant solution and the Tan $\delta_{dielectric}$/Tan $\delta_{solvent}$ ratio possesses greater relevance. If multiple turnovers are not desired (i.e., a reaction that is less than or equal to stoichiometric), the dielectric can be removed from the solvent prior to microwave radiation. Thus, when microwaving in air, for example, the Tan $\delta_{dielectric}$/Tan $\delta_{solvent}$ ratio becomes irrelevant.

There are numerous instrument formats that can be successfully applied to the invention. These can be describes separately:

a) the microwave source. As described above, there are many devices that generate microwaves—most notable for the present invention are magnetrons and solid-state devices. Low power magnetrons (500-1200 W) commonly found in kitchen microwave ovens are sufficient for the invention.

Alternatively, solid-state devices, such as Bluetooth or Wi-Fi chips, are commonly used in wireless communication devices. They emit low power (>1 W) microwaves at essentially the same frequency as kitchen microwave ovens (2.45 GHz). These devices are much smaller than light-bulb-sized magnetrons—they are roughly the same size as a house key. Hence, solid-state devices can generate microwave power in a handheld device. The low power levels are sufficient for use in this invention, especially if the dielectric heats well and if the sample to be heated is placed in a waveguide (see below).

(b) integration or non-integration of the dielectric into the reaction vessel. The dielectric to be heated is in proximity to the biomolecule that undergoes an analytical reaction. It is often convenient to integrate the dielectric into the reaction vessel (i.e., a dielectric-containing microarray chip). However, it is a viable alternative to have the dielectric separate from the reaction vessel. For example, a dielectric-containing microchip holder could be included into the design of the microwave instrument. A microarray chip to be analyzed would not contain dielectric but would be inserted into the holder. Critical to the design is that the dielectric must be in thermal proximity to the surface of the solid support where the biological reaction/analysis occurs.

(c) location of sample insertion (Waveguide or Oven Cavity). As mentioned above, the solid support (reactants) and dielectric may absorb microwave energy in an oven cavity or in a waveguide. Advantages to irradiation in a waveguide rather than an oven chamber include (a) a more uniform microwave bath (no hotspots from standing waves), and (b) a greater fraction of the generated microwave energy actually strikes the sample (more concentrated power absorption). Another advantage is that a waveguide is generally smaller than an oven cavity, which is advantageous when instrument size is an issue.

2) The dielectric material: As described in 1), for aqueous reactions it is desirable to use dielectric materials that have higher loss tangents than the solvent (if catalysis is desired). A list of materials that have higher values of Tan $\delta$ than water (as a solvent) is shown below. All of these materials (and others not listed) can be used in the invention (note: investigator-to-investigator differences are usually due to differences at which the data were collected):

TABLE 2

| Frequency | Tan$\delta$ × $10^4$; water | Tan$\delta$ × $10^4$; ethylene glycol |
|---|---|---|
| 3 GHz | 1570 | 10,000 |

Effect of Microwave Heating on Temperatures of Solids—1 Min Heating:

| Water: | (560 W, 2.45 GHz oven) 81 C. |
|---|---|
| Carbon: | (500 W, 2.45 GHz oven) 1283 C. |
| Nickel: | (500 W, 2.45 GHz) 384 C. |
| Copper oxide: | (500 W, 2.45 GHz) 701 C. (0.5 min heating) |

| Material* | Tan$\delta$ 915 MHz | Tan$\delta$ 2450 MHz |
|---|---|---|
| barium titanate | 0.20 | 0.30 |
| clay (20% water) | 0.47 | 0.27 |
| manganese oxide | 0.09 | 0.17 |
| water | 0.043 | 0.12 |

*Buffler and Risman, 1996

A material with a high dielectric constant is barium titanate ($BaTiO_3$). The dielectric constant is 200-16,000 (compared with 80 for water). Barium titanate can be formed into films and has been used in analytical devices (Ewart et al, U.S. Pat. No. 5,922,537). Moreover, in addition to barium titanate, methods for forming thin and thick films of other ferroelectric materials at low temperature have improved steadily. Known high dielectric constant inorganic titanates, niobates, and ferroelectric polymers can be formed by many processes including low temperature chemical vapor deposition, laser photo-ablation deposition, sol-gel processes, RF magnetron sputtering, screen printing and firing, (in the case of the polymer) spin coating, and other methods (Yang et al., 1998).

Natural clay can also be used as a moldable dielectric (see tables above). In addition, a 1:1 w/w mixture of alumina-magnetite ($Al_2O_3$—$Fe_3O_4$) can be used as a dielectric support that heats strongly (Bram et al., 1991). Magnetite ($Fe_3O_4$) particles by themselves heat well under microwave irradiation. Clay differentiates itself from water as a microwave absorber at 915 MHz much more than at 2450 MHz (compare in Table above).

Another material that could be used is carbon. Forms of carbon include carbon black, activated charcoal, graphite, carbon nanotubes and nanospheres (such as $C_{60}$ and $C_{70}$). The use of carbon as the dielectric is described elsewhere in this document.

Many additional dielectric materials can be identified by screening dielectrics for their ability to heat substantially faster than solvents such as water during microwave irradiation. Class I dielectrics (dielectric constants typically less than 150) and Class II dielectrics (dielectric constants typically in the range of 600-18,000) can be used (technical brochure, Novacap, Inc., Valencia Calif.). Other suitable materials include organic polymers, aluminum-epoxy composites, and silicon oxides. The microwave frequency can be varied as well. This simple screening procedure would yield conditions (frequency and material) that would direct heating toward the dielectric material without substantially heating water. Indeed, a company, Symyx Technologies, Inc. (www.symyx.com) routinely carries out combinatorial synthesis of novel materials to discover those with attractive qualities such as unique dielectric properties (Schultz et al., U.S. Pat. No. 5,985,356).

Still other materials that heat substantially under RF irradiation include ferrites and ferroelectrics. In addition to $BaTiO_3$, described above, other Perovskites (minerals of the chemistry $ABX_3$) such as $NaNbO_3$, $LaCoO_3$, $LaSrO_3$, $LaMnO_3$, and $LaFeO_3$ heat well in a microwave field. Other materials that heat efficiently in a microwave and which could be used in the invention include SiC, AlN, ZnO, MgO—SiC, $Al_2O_3$, and AlN—SiC.

Other types of materials that are well known to heat dramatically under microwave irradiation are various ceramics; oxides ($Al_2O_3$, for example), non-oxides (CrB and $Fe_2B$, for example), and composites ($SiC/SiO_2$, for example). Numerous materials are processed (sintered, etc.) by exploiting their microwave heating characteristics. (National Academy of Sciences USA, 1994).

Microwaves can heat composite materials. For example, materials that are normally transparent to microwaves can be heated by adding polar liquids or conducting particles. Refractory oxides such as alumina, mullite, zircon, MgO, or $Si_3N_4$ have been made to couple effectively with microwaves by the addition of electroconductive particles of SiC, Si, Mg, FeSi, and $Cr_2O_3$. Oxides including $Al_2O_3$, $SiO_2$, and MgO have been effectively heated by the addition of lossy materials such as $Fe_3O_4$, $MnO_2$, NiO, and calcium aluminate. Mixtures of conducting powders, such as Nb, TaC, SiC, $MoSi_2$, Cu, and Fe, and insulators such as $ZrO_2$, $Y_2O_3$, and $Al_2O_3$, have coupled well with microwaves. Various materials in solution (zirconium oxynitrate, aluminum nitrate, and yttrium nitrate) that are good couplers have also been added to enhance microwave absorption of powdered insulating oxides. A microwave absorbing heating mantle is sold by Milestone, Inc. made from a composite of graphitic carbon and Teflon.

Addition of conductive materials in various shapes including powder, flake, sphere, needle, chip, or fiber, would cause the heating of low loss materials. For example carbon black or metal pieces with sizes ranging from 0.1-100 µm can increase the heating properties when used as inclusions. The nature and concentration of such materials can be optimized without undue experimentation (Committee on Microwave Processing of Materials et al., 1994).

As mentioned above, it is known that ceramics can have piezoelectric properties. It is also known that piezoelectric materials can be used to accelerate binding of a biomolecule to a surface or to another biomolecule through sonication (Sizto & Gallup, 1986; Wohlstadter, et al., 2002). Thus, by giving the microwave-targeted dielectric ceramic electrical connections (a skill known in the art), it can double as both an ultrasonic vibrating/buzzing piezoelectric to accelerate binding and as a heating element to accelerate an analytical reaction.

3) The reaction carried out can be virtually any chemical reaction in which the reactant(s) can be bound to a specific binding reagent. These include all known enzyme-catalyzed reactions and all known zeolite reactions. The invention may be used to carry out reactions not know to be catalyzed by natural catalysts. The key features are: (1) the reactant(s) be able to be specifically bound, and (2) the reaction be accelerated by heat.

Also contemplated are microwave-accelerated chemical reactions that prepare the surface for the specific reaction to be microwave accelerated. One example is the preparative adsorption reaction between a protein molecule and a plastic surface. Another example is the stepwise synthesis of a peptide, single-stranded nucleic acid, or small molecule ligand.

Although not actually a preparative reaction, microwave heating of the dielectric can be used to inactivate any harmful organisms (viruses, bacteria) or biomolecules that remain after an analysis. For example, a dielectric chip or microtiter plate could be microwaved to a high temperature or for a long time after an analysis to ensure biohazardous waste is diminished or destroyed. This is a safety feature of the invention.

Microtiter plates are in common use to perform biological analyses (Johnson, 1999). They typically have 96 wells in an 8×12 array, but can also have other configurations and numbers of wells including 24, 384, and 1536. They are (usually) disposable devices made of acrylic or polycarbonate, but can be made of essentially any material. The volumes of the wells vary depending on the number of wells per plate, but 96-well plate wells hold roughly 150 microliters of liquid. Immunoassays including ELISAs, enzyme assays, and nucleic acid assays are commonly performed in wells. Most often, a different assay is performed in each well (1:1), although it is becoming increasingly common via low-volume reagent spotting technologies (e.g., Cartesian Technologies, Inc. (Irvine, Calif.), BioDot, Inc. (Irvine, Calif.)) for multiple assays to be carried out in a single well. For example, if a 4×4 array of assays is carried out in each well of a 96-well plate, 1586 assays can be performed in the plate (16×96). Typically, plates are prepared for analysis by coating the interior surface of the wells (entirely or by array spotting) with a specific capture molecule, such as an antibody. Binding usually occurs by non-specific absorption. Incubation of plates at elevated temperatures accelerates the surface coating process; incubation at 37° C. for 30 minutes is roughly equivalent to incubation at 20° overnight. Because binding is a surface phenomenon and bulk heating may denature biomolecules in the aqueous solution of the wells, it is preferable to target heating to the well surfaces. This can be done by microwave heating microtiter plates that have dielectric in thermal proximity to the well surfaces. This can be accomplished by coating the plate bottoms with dielectric, for example by painting, or by incorporating dielectric into the plate material (plastic). Alternatively, conventional plates may be placed in a holder or mantle that contains dielectric material. In all cases, the dielectric is in thermal proximity to the surface where biomolecule attachment occurs. The extent of well coating can be measured by standard means known in the art, such as total protein or DNA determination using colorimetric or fluorescent reagents. Coating can also be analyzed by a function-based assay (see Example 11). Once the well is coated with the molecule of choice, an analytical reaction can occur (DNA probe assay, immunoassay).

Another type of preparative reaction that can be performed is a chemical (organic or inorganic) synthesis. The synthesis may be of a single compound or an array of different compounds, particularly an array prepared via combinatorial chemistry (Gallop, 1994; Gordon, 1994; Jacobs & Fodor, 1994; Dolle, 2000). The compound or compounds can subsequently be used in a biological assay. For example, a biological receptor can be added to the chemical array and an assay can then be performed to detect receptor binding to any of the synthesized compounds. This is type of experiment is characteristic of the fields of "chemical genomics" and "chemical proteomics". Although, there are many formats for combinatorial chemistry, of particular importance in this invention is combinatorial chemistry on a microchip. Small-scale chemistry enables low-cost screening of libraries of compounds. Synthesis on a microarray chip also obviates the generation of large volumes of organic solvents and other hazardous waste. Microwave-assisted synthesis of compounds on a chip in preparation for analysis on the same chip has until now not been performed or contemplated. Reports of microwave-assisted combinatorial chemistry have been published (Kappe, 2001; Borman, 2001) and combinatorial chemistry on chips has also been reported (Fodor et al., 1993; Kramer & Schneider-Mergener, 1998; MacBeath et al, 1999; Hergenrother, 2000; LeProust, 2000, Korbel, 2001; Graffinity Pharmaceutical Design, Heidelberg, Germany; Xeotron Corp., Houston, Tex.). Due to the concept of thermal proximity of the dielectric to the solid support (the micro array chip or microtiter plate) the present invention enables for the first time solid phase chemical synthesis on a support. Moreover, the thermal proximity of the dielectric further allows, not only surface chemical synthesis, but also subsequent microwave-directed heating in a surface analytical reaction (e.g., a microwave-triggered chemiluminescent reaction on a microarray chip or microtiter plate).

4) The reactant binding molecule can be any molecule that is capable of specifically interacting the reagent(s). If more than one turnover is required, then the binding molecule should also be heat stable. If it is not heat stable then microwave heat should not be applied until after a time has elapsed to allow sufficient turnover to occur. The molecule may be low or high molecule weight, natural or manmade. Typical binding molecules could be antibodies, enzymes, receptors, nucleic acids, molecularly-imprinted polymers, and zeolites. These molecules have specific binding pockets or crevices. Alternatively, molecules could be immobilized that do not have binding pockets but are recognized specifically by molecules with binding sites. These include enzyme substrates, enzyme inhibitors, receptor ligands, and receptor antagonists. Any of a variety of modes of attachment to the dielectric can be employed. For example, molecularly-imprinted polymers can be polymerized around dielectric beads or particles. Molecularly imprinted polymers can be formed as thin layers on surfaces (Shi et al., 1999; Glad et al., 1985; Kempe et al., 1995; Burow and Minoura, 1996; Mathew-Krotz and She, 1995; Dai et al., 1999; Norrlow et al., 1984). Zeolite crystals can be grown on dielectric surfaces or be coated by the technique of dip coating (van Bekkum et al., 1994; Jansen et al., 1994). Proteins and nucleic acids can be coated non-specifically to numerous surfaces. Small molecules may be attached via tethers or entrapped in porous supports, with or without microwave-induced reaction acceleration.

5) The physical format of the reaction vessel. Although not critical to the practice of directed microwave chemistry, there are preferred types of solid phases on which reactions occur. In terms of shape formats, biological reactions are most frequently carried out on chips (or slides), microtiter plates, test tubes, centrifuge and microcentrifuge tubes, and beads. The key features are that the solid support must have a surface on which biomolecules are affixed and where biochemistry takes place, and the surface must be in thermal proximity to a microwave-heated dielectric material.

There are three preferred ways in which the dielectric material can be in thermal proximity to the reaction surface. First, the dielectric can be incorporated into the material that makes up the solid support. For example, a composite of Teflon and graphite or barium titanate can be made (Milestone, Inc., Monroe, Conn.). Microarray chips or microtiter plates can be extruded or injection molded from the composite. Second, the dielectric can be attached or deposited as a coating or layer on the solid support. The dielectric can be painted or spotted to the underside of a chip or plate (for example, as a barium titanate or carbon paste). It can also be included within a chip as a "sandwich" layer. Third, the dielectric can be a solid mantle or holder on/into which the solid support is placed prior to reaction. In this third format, a chip or plate can be disposable but the dielectric mantle can be reused. A dielectric mantle also allows the dielectric material to have substantial mass (many grams), which facilitates rapid microwave heating.

6) The detection method may be any method that detects a physicochemical change that accompanies a microwave accelerated chemical reaction. The detector may detect light emission, color change, fluorescence changes, mass changes, etc. The detector is preferably integrated with the microwave reaction, such as a PMT, CCD camera, photodiode array, or x-ray film to detect light emission, for example in chemiluminescence reactions. Similarly, a laser or tungsten or incandescent lamp can be used together with a light detection device (PMT, etc.) to detect absorbance or fluorescence changes.

Preferred Methods and Compositions of Matter

There are numerous ways of practicing the present invention. Some variables include: altering the microwave frequency and power, the identity of the microwave susceptible material, the reaction surface shape (planar or spherical), the reagent capture mechanism (antibodies, DNA, covalent, non-covalent, etc), and the identity of the reaction to be accelerated, and practical applications (analytical, bioanalytical, preparative, etc.). Described below is a brief overview of some variables and their practical application. Also described are the current best ways of carrying out the microwave accelerated targeted reactions.

One highly attractive format for the invention is to use it on "chips," i.e., disposable planar surfaces, often made on microscope slides (for example, 1×3 inch rectangles of glass or 5 inch×5 inch plates of glass). Another attractive format is to use it on "microtiter plates". Spotting using inkjet printing or other high-resolution deposition methods results in from one to thousands of reaction spots on the surface of a chip or one to several (e.g., a 4×4 array) spots within an individual microtiter plate well. There are numerous manual and automated means of spotting known in the art. Numerous commercial suppliers exist that sell spotting robots (Biodot, Cartesian) as well as simple inexpensive devices for spotting (Xenopore). Small volume analyses on such so-called "microchips" (Schmalzing et al., 2000) enable huge numbers of assays to be performed on a single chip. Arrays ("macroarrays" or "microarrays") on chips or in microtiter plates can be used for analytical purposes. Thousands of assays can be performed on a single chip or plate using deposition technologies know in the art, which are commercially widely available (Pasinetti, 2001; Lennon, 2000; Cooper, 2001; Draghici, 2001; Zubritsky, 2001). For example, an array of spots can be used to detect genetic mutations in a myriad of genes. Another example is an immunoassay, in which an antibody would be present in a spot. Another example is a ligand assay in which small molecule such as an alkaloid or a peptide would be present to capture a specific protein receptor. Chips and plates can be used in numerous analytical applications including but not limited to; biochemical research, medical diagnostics, water testing, food pathogen testing, and chemical/biological warfare agent testing.

In an addition or alternative to analytical uses, surface-targeted microwave heating can be used preparatively. Extending the application of microchips and microtiter plates described above, the chips and plates could be prepared for subsequent analytical use using directed microwave reactions. One general area is the use of targeted microwave heating to enhance capture protein binding to plates or chips. Another general area is to use targeted microwave heating to accelerated on-chip or on-plate synthesis of small molecule compounds such as peptides or alkaloids.

In terms of using directed microwave heating to aid on-chip or on-plate organic synthesis, the invention is attractive for preparation of miniature combinatorial chemistry libraries (Dolle, 2000). Numerous unique chemical compounds can be synthesized in situ on chips. For example, thousands of different peptides can be prepared by conventional solid phase procedures on a chip. The combinatorial chemistry chips can then be used analytically to assay the solid phase chemical libraries. For example, the chip can be exposed to a solution of chemiluminescently labeled enzyme solution and binding can be detected. Such an assay format can be used to discover enzyme inhibitors. Similarly, receptor binding to combinatorial libraries of potential ligands can be conducted. Microwave irradiation can be used to accelerate on chip library synthesis and, later, to analyze the chip (for example by microwave-induced chemiluminescence).

The chips (or alternative dielectric surface) can also be coated with material for solid phase extraction of analytes from a bulk solution. Solid phase extraction can be non-specific (adsorption), immunoabsorption, or by using molecularly-imprinted polymers (Fleisher & Boos, 2001; Krishnan & Ibraham, 1994).

Many attractive potential uses of microwave targeted reactions are in the fields of biotechnology/medicine. In these cases, measured analytes have biological function. Any conventional assay such as an immunoassay or a DNA probe assay can be carried out by the described technology. In these assays, well-known chemical conversions would occur causing a detectable physicochemical change in some label. For example, chromogenic, fluorogenic, or luminescent reactions could be carried out.

Yet another assay format that could be used is molecular beacon technology (Robinson et al., 2000). With molecular beacons, hybridized strands of nucleic acid are detected by fluorescence emission and quenching by end-labeled nucleic acid probes. One end has a fluorophore, the other a quencher. Upon hybridization the ends separate and fluorescence is detectable. Using microwave heating, the probe could be released back into solution at a temperature. The temperature of separation (melting temp) could be determined by fluorescence quench upon release. The most attractive detection format is chemiluminescence (CL). These are described in greater detail below in the section delineating sample practical applications in medicine.

A preferred way of conducting the procedure is to use carbon particles as the dielectric. Carbon may be activated carbon/charcoal (Sigma-Aldrich Chemical Co.), carbon black (Columbia Chemicals, Marietta, Ga.; Reade Advanced Materials, Providence, R.I.), graphitized carbon particles (Polysciences, Inc. Warrington, Pa.) or dextran-coated charcoal beads (Research Diagnostics, Inc.). Preferably the carbon beads are coated with a polymer that is imprinted with the reactant (ideally, polymerized around the carbon).

It is often desirable to accelerate the specific reaction of a single chosen chemical in the presence of other non-chosen chemicals. In a preparative chemistry example, in drug manufacture it is often desirable to accelerate a chemical reaction (for example, ester hydrolysis) of one enantiomer in the presence of a mixture of types of molecules (for example, a bulk racemic mixture). In an analytical chemistry example, in medical diagnostics it is desirable to accelerate a specific chemical reaction to signal the presence of one specific type of molecule in a vast milieu of other types of molecules. The present invention provides an improved means of accelerating specific chemical reactions, and as such has many practical applications in both preparative and analytical chemistry.

Reactions of analytical utility include those that result in a change in color, luminescence, fluorescence, electrochemistry, or any other detectable physical property. Preparative reactions include hydrolysis and/or enantioselective reactions, etc. Any preparative reaction in aqueous or organic solution is amenable to the described invention. As with analytical applications, preparative reactions can be monitored by changes in color, luminescence, fluorescence, or any other detectable physical property.

A preferred reaction is the chemiluminescent reaction between luminol and hydrogen peroxide. As described below, this reaction is a well-known signaling reaction used in various fields such as medical diagnostics and biomedical research. The reaction is temperature dependent and can be slowed to appropriate temperature control by adjusting the pH to a point lower than optimal (see Examples 9 and 10).

Chemiluminescence reactions, such as the luminol-peroxide reaction, can be monitored and quantitated in many ways including the use of film (for example, X-ray film), or electronically using a photomultiplier tube (PMT) or a charge-couple device (CCD) camera. A PMT-based instrument would involve a microwave-emitting device with a window through which light is measured. Measurement using a PMT or a CCD camera would be collected and analyzed using a personal computer and conventional commercial data acquisition/analysis software (for example, LabVIEW). Currently a preferred method involves the use of film.

As described above, the dielectric material can be in various formats. Currently the most attractive format is on a chip, either as spots or as a layer. The use of a "dielectric chip" allows sensitive detection of multiple analytes. Indeed, microarray chips or microchips are an attractive application of the invention.

Description of Illustrative Practical Applications

There are numerous practical applications of targeted triggered microwave reactions. Many are in the fields of analytical and preparative chemistry. Some though, are in non-analytical fields. For example, a reaction could be directed at a toxin (such as a nerve gas) to specifically inactivate that toxin. The described invention could be useful in any practical application where a chemical reaction is desired and it is important that that reaction is specific for the chosen molecule.

Very attractive applications are in the biomedical analysis. Analyses of biomolecules are critical to diagnostic/prognostic evaluations. Moreover, scientific research depends on the ability to detect and measure specific biomolecules. Such biomolecules include but are not limited to proteins (immunoassay detection) and nucleic acids (hybridization detection).

The invention discloses how targeted microwave heating can be used to accelerate analytical reactions that occur on or in thermal proximity of surfaces. It also discloses how microwave heating can accelerate reactions that modify surfaces in preparation for subsequent analytical reactions.

Comparison with Alternative Analytical Technologies

Microwave-accelerated chemiluminescence (CL) analysis in a medical or research setting has several advantages over commonly used technologies. Microwave-accelerated CL-based analysis on chips is termed herein as "Microwave Accelerated, Targeted, Triggered Reaction" technology (MATTR).

MATTR has clear advantages over existing methods. There are two types of comparable technologies;

First are mainstream chemiluminescent analytical technologies (Bowie et al., 1996; Roda et al., 2000). Companies marketing these technologies include Tropix (subsidiary of PE Corp.), which sells enzyme-based CL reporters, and Amersham Pharmacia Biotech, which sells CL-based gel blotting detection systems. Other companies with conventional CL-based products include Lumigen, Lifecodes, Vector, Invitrogen, and Pierce. The attractiveness of MATTR over conventional analytical CL methods can be seen in Table 3. CL reactions are generally either "flash type" or "glow type". Flash-type reactions are instantaneous and hence demand fast reagent mixing and analysis. Glow-type CL reactions emit low levels of light over a long time period (minutes or hours).

TABLE 3

Comparison of Flash and Glow CL reactions to MATTR-based CL reactions

| Flash | | Glow | | MATTR | |
|---|---|---|---|---|---|
| Advantages | Disadvantages | Advantages | Disadvantages | Advantages | Disadvantages |
| Rapid time to answer | Timing of injection, read | Substrate addition non-critical | High temperature dependence | Substrate addition non-critical | Requires microwave source |
| High-throughput | Mixing critical | Signal can be adjusted for different enzyme levels | Amplifies background & non-specific binding | High-throughput | |
| High signal-to-noise | Photon counting more difficult | Read time can be adjusted to increase high-throughput | Signal generation is affected by assay additives | High signal-to-noise | |
| Low temperature dependency | Difficult to engineer signal variations | Easy to engineer | Stable signal can take hours | Easy to engineer | |
| Linear response | | Samples can be sequentially read | | Linear response | |
| Wide dynamic range | | | | Wide dynamic range | |

Figure 3:
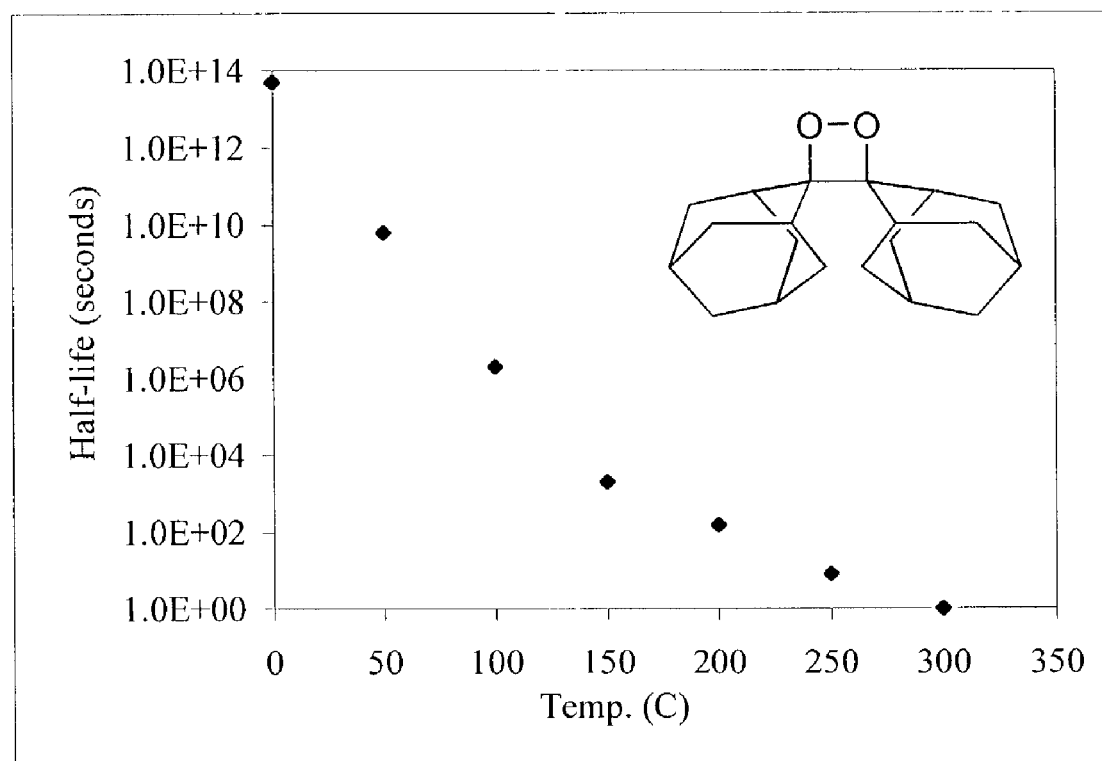
FIG. 3: Half-life of Adamantylidene adamantine 1,2-dioxetane versus temperature. The figure illustrates the strong dependence of the dioxetane half-life on temperature (dioxetane breakdown initiates CL). Note that the abscissa scale is logarithmic.

A typical glow type reaction involves the hydrolysis of chemiluminescent dioxetane compounds. As shown in FIG. 3, hydrolytic dioxetane luminescence is highly temperature dependent. Thus, dioxetanes make excellent MATTR labels. A typical flash type reaction involves chemiluminescent acridinium esters. The flash of CL of acridinium esters is chemically triggered upon mixing with chemical initiators. The reaction rate is slowed to an imperceptibly slow rate by lowering the initiator concentration. Microwave heating restores the rapid reaction rate causing a chemiluminescent flash (Wood, 1984).

MATTR technology fulfills several criteria, which distinguish it as a breakthrough bioanalytical technology and as a significant improvement to conventional CL-based bioanalyses:

A CL technology that offers signal generation "on demand" (electronically, not by reagent mixing). In MATTR, microwave energy is applied on demand, conveniently allowing CL reactions to be triggered electronically rather than by rapid physical mixing.

A physically simple analytical instrument to reduce costs and minimize maintenance. MATTR requires microwave input, which is diffuse and thus simpler than technologies that require focused light input (fluorescence or spectrophotometry).

Highly sensitive and extremely rapid analysis. Rapid, targeted microwave heating caused by causes a burst of CL light, using well-established highly-sensitive CL chemistry.

A technology capable of multiplexed, microchip-based assays. Microwave heating can be spatially directed, e.g., to specific areas on a microarray chip by patterned dielectric spots. A broadly enabling technology, useful for many types of assays. Because MATTR incorporated well-established luminescent labels, it will be able to be used in all formats of conventional CL, as well as more. It promises to be useful in immunoassays as well as DNA probe assays.

MATTR Instrumentation in Biomedical Analyses

Figure 4:
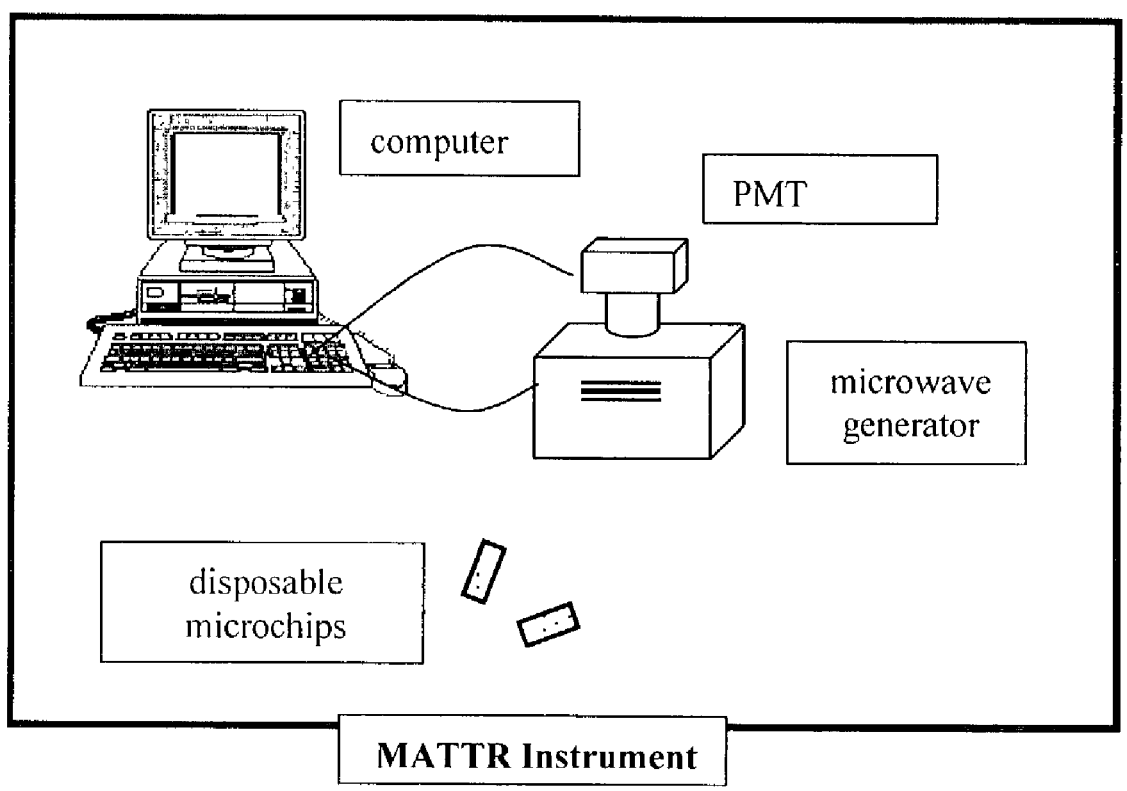
FIG. 4: A Microwave Accelerated Targeted Triggered Reaction ("MATTR") instrument. The components of the instrument are a microwave oven with a built-in holder for MATTR disposable chips. The chips emit light upon microwave heating, which is captured by a PMT (either directly through a window or via fiber optics) or a CCD camera. Microwave generation, camera recording, and image analysis are all carried out using a PC. Alternatively, light could be captured on autoradiography film, obviating the need for an electronic imaging device and computer.

As described above, CL from a MATTR chip could be measured on film or electronically (using a PMT or CCD camera). If a PMT or camera is used, a "MATTR instrument" is employed. The basic components of a preferred MATTR instrument are shown in FIG. 4. The preferred instrument includes a microwave oven with a window through which chip-emitted light is detected by a PMT or camera. Onset of microwave irradiation (acceleration of CL reaction), light measurement, and data analysis are carried out, for example, using a standard PC with appropriate software. Suitable data acquisition/analysis software is common and known in the art.

One type of MATTR instrument that can be made to measure cytokines on chips is described here;

a suitable microwave oven is made from a microwave moisture/solids analyzer (model M2, Denver Instrument Co., Arvada, Colo.). The oven will preferably have a single mode microwave chamber to provide a uniform power density. The microwave chamber of such an oven is small and cylindrical and the energy is focused on the sample. The operating frequency of microwave emission will be 2450 MHz. The output power of the microwave will be 550 W. The power source will be 115 V, 60 Hz.

The interior of the oven chamber will be fitted with a chip holder that is aligned with the fiber optic cables. The fiber optics will run from the interior of the microwave to a PMT on the exterior of the oven. The chip holder will support disposable dielectric assay chips of various sizes (for example, from 1×3 inches up to 5×5 inches).

A fiber optic detection system to allow chip imaging within the microwave chamber. Fiber optics will lead from the chip to a light-recording photomultiplier tube (PMT, Hamamatsu model H5784-01), which captures light emitted light from the CL reaction, and a personal computer will preferably control and synchronize the PMT and the microwave source. The computer will also preferably run a versatile data acquisition, control, analysis, and presentation software package, such as LabVIEW software (National Instruments Corp.).

MATTR Chemiluminescent Compounds for Bioanalytical Assays

There are very many chemiluminescent reactions known which efficiently emit light and can be used for bioanalytical purposes. Some classes of CL reactions are (each of which has many structural variations); 1,2-dioxetanes, aryl oxalates, acridinium esters, luminols, and lucigenin. All of these classes have been used analytically, either as labels in immunoassays or as chemiluminescent enzyme substrates. In most cases, the light-emitting chemical reaction that occurs is a bimolecular reaction, often with an oxidizing agent. Hydrogen peroxide and sodium hydroxide are common second reagents. All of the reactions may be accelerated by an increase in temperature. There are vendors of these compounds such that both free CL compounds as well as CL compounds labeled with linkers for protein modification for use in immunoassays.

One type of CL reactant class that is very useful in MATTR CL reactions is 1,2-dioxetane reactions. Dioxetanes emit light without any secondary reagent such as hydrogen peroxide. In addition, dioxetane CL reactions are remarkably temperature dependent as is shown in FIG. 3. Dioxetanes are used as glow type regents in enzyme immunoassays and enzyme assays of alkaline phosphatase, glucuronidase, glucosidase, and beta-galactosidase (Tropix, Foster City, Calif.). As can be seen from FIG. 3, they can be converted from glow type reagents to flash type reagents by the use of elevated temperature. Various dioxetanes are commercially available from Tropix and other sources and methods for conjugating them to proteins have been published. In addition, Tropix sells conjugates, which can be linked to proteins.

Acridinium esters are another class of CL reagents that is useful in MATTR. These compounds react with acids and bases in the presence of an oxidizing agent, resulting in flash type CL. Several acridinium esters are commercially available. Lumigen, Inc. (Southfield, Mich.) sells small, water-soluble chemiluminescent labeling acridinium esters that are triggered by a simple chemical reaction to produce CL as a rapid flash. The compounds are modified to permit covalent attachment to proteins, nucleic acids, and other biomolecules. The chemical kinetics of these compounds can be slowed by judicious dilution of the triggering reagents. Flash CL will be restored upon microwave heating. Another company, Assay Designs, Inc. (Ann Arbor, Mich.), also sells acridinium ester labeling kits. Their acridinium esters link to proteins via NHS ester functional groups. Assay Designs also sells trigger solutions to affect light emission.

MATTR Chip-Based Immunoassays

Figure 5:
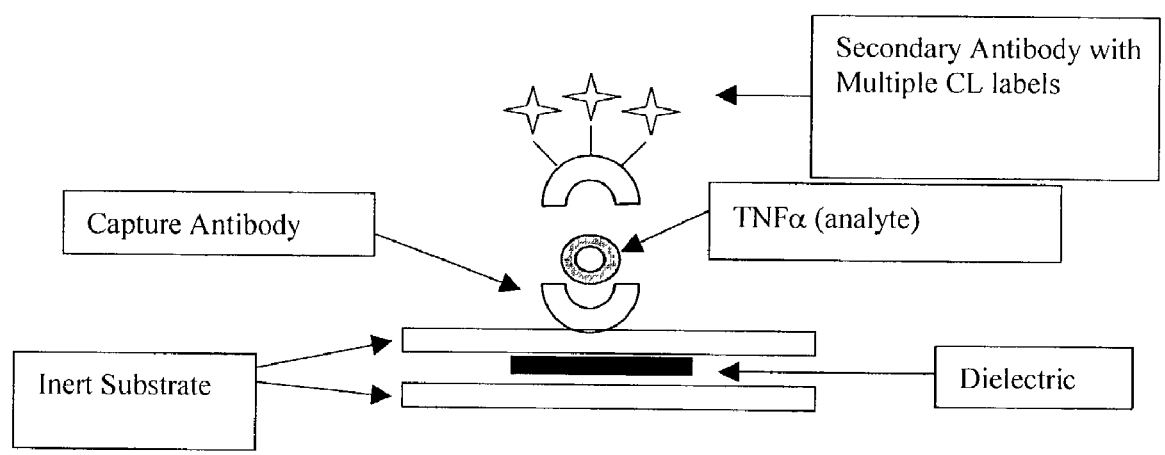
FIG. 5: MATTR-based sandwich immunoassay TNFα immunoassay. Upon microwave heating, light emission from multiple CL labels signal the presence of the analyte, TNFα.

MATTR-based immunoassays may be conducted in any of a wide variety of formats. For example, a MATTR chip, with specific capture molecules on it surface, may be exposed to analyte solution, followed by secondary antibody binding (if necessary), and washing (if necessary) (FIG. 5). Immunoassays are performed using either competitive or sandwich immunoassay formats. The signaling label, a low molecular weight chemiluminescent reporter molecule, will be present on the appropriate surface-bound molecule. Once the binding and washing has been completed, the chip is placed in the MATTR instrument and analysis is carried out.

Immunoassay Detection of Angiogenic Growth Factors

One application of MATTR technology is in the immunoassay-based detection of cancer-related angiogenesis proteins. Angiogenesis, also called neovascularization, occurs in the healthy body during wound healing, in the female monthly reproductive cycle, and in pregnancy. Angiogenesis is controlled in the body through a series of "on" and "off" regulatory switches—the main "on" switches are known as angiogenesis growth factors (cytokines) while the main "off" switches are known as endogenous angiogenesis inhibitors. In the healthy body, there is a balance between angiogenic and anti-angiogenic factors such that blood vessel growth is appropriate.

Tumors express large amounts of angiogenic growth factors to recruit their own blood supply. Solid tumors require a constant vascular supply, which allows cancer cells to maintain their growth advantage. Because of the relatively large amounts of angiogenesis factors secreted by tumor cells, tumor vasculature is abnormally wide lumens, irregular blood flow, regions of stasis, and high permeability. There are many different angiogenic proteins, making them attractive for multi-analyte chip based detection and measurement. Analysis of angiogenic factors is important in biomedical research and in diagnosis on treatment of various diseases, including cancer.

Anti-angiogenic therapy offers a promising anti-cancer strategy (Folkman, 1997). Angiogenesis inhibition would prevent further vessel growth and reduce metastasis, and hence inhibit tumor growth. This philosophy is being widely pursued. Currently an amazing diverse group of over 20 anti-angiogenic drugs are undergoing evaluation in clinical trials (Saaristo et al., 2000) with many more in various stages of research and development.

An example of an immunoassay is one for tumor necrosis factor alpha (TNFα). TNFα is an angiogenic growth factor protein. There are several commercial sources of high quality required reagents, TNFα and appropriate antibody pairs. R&D Systems (Minneapolis, Minn.) sells a CL-based assay for this protein that could be used in a MATTR based assay. The assay is a sandwich enzyme immunoassay. With MATTR, the secondary antibody is labeled with multiple copies of a chemiluminescent compound by means known in the art.

A typical MATTR assay of TNFα would use a barium titanate/glue composite undercoated microscope slide as the chip. Binding of reagents can be carried out without undue experimentation using reagent vendor's instructions (R&D Systems, Minneapolis, Minn.; Sigma Chem. Co., St. Louis, Mo.). Anti-TNFα antibodies (matched set), wash buffer, and blocking buffer are sold by R&D Systems. First, mouse anti-human antibody is immobilized on the chip by spotting. After blocking, Human TNFα (R&D Systems) is added and allowed to bind. To captured TNFα is added biotinylated detection antibody (goat anti-human) to which isoluminol-streptavidin (Sigma Product S8532, 3.5 isoluminol molecules per streptavidin) has been allowed to bind. The complete chip-bound sandwich complex (antibody-TNFα-antibody-streptavidin/isoluminol) is detected by MATTR by adding neutral peroxide and microwaving. Emitted light is detected by any of various means including autoradiography film, photomultiplier tube (PMT), or charge-coupled device (CCD) camera.

MATTR Chip-Based Nucleic Acid Probe Assays: Cancer Cell Gene Expression Analysis Another practical application of microwave-accelerated chemiluminescence on dielectric chips is in nucleic acid detection of cancer cells. Molecular oncology is increasingly moving toward the use of multiple biomarkers for diagnostic, and prognostic purposes (Sidransky, 1997; Abati & Liotta, 1996; Marx, 2000). The understanding of how individual tumors grow and respond to treatment is based on an understanding of how cellular molecules interact to affect cell growth, metastasis, and response to anti-tumor agents. Because cancer is a highly individual disease—it is not one disease but hundreds—it will become extremely valuable in the future to be able to detect, not just one or two tumor markers, but a large number simultaneously. The field of personalized oncology hinges on two features; 1) an understanding of the intricate molecular roles of cancer proteins, and 2) the ability to detect and measure the many key molecules, which determine the individual characteristics of tumors. MATTR can play an important role in both aspects; MATTR chips may help researchers map the pathways of tumors, and provide physicians with critical information needed to effectively custom-treat a cancer patient. In the long term, a potentially important role exists for MATTR-based gene expression profiling in cancer screening, diagnosis, staging, surveillance, and treatment monitoring.

MATTR can be applied in the detection of assay panels in cancer staging. After cancer is diagnosed, the extent or "stage" of the cancer is determined before deciding on a treatment plan. Tests are performed to determine tumor staging (size/extent of tumor), node staging (involvement of lymph nodes), and metastasis staging (presence or absence of metastasis). Staging is performed in part with the use of molecular testing for tumor cells in blood and sentinel nodes. Tumor staging is a very attractive application of MATTR array testing because it allows physicians to determine treatment strategies, particularly about whether or not to prescribe adjuvant therapy.

A second foreseeable nucleic acid diagnostic application of MATTR chips is the detection of minimal residual disease (MRD). Decision of treatment would be greatly enhanced by a multi-analyte cDNA panel showing able to detect circulating cancer cells at low levels undetectable by other methods. Using MATTR, some patients in clinical and pathological remission will show evidence of "molecular disease", which has clear diagnostic and therapeutic implications. Molecular diagnostics has great potential in identifying MRD.

It is clear that future testing will involve detection and measurement of arrays of cancer-associated biomarkers. Multi-analyte panels have clear advantages over single analyte testing. With multiple markers, there is much less chance of false positives/negatives. In addition, perhaps most importantly, is that multiple biomarkers will give a clearer and more complete picture of the tumor's characteristics. For example, the likelihood of drug resistance or metastatic potential could be confidently determined. In most cancers, the ideal panels for these determinations have yet to come into focus. MATTR chip technology can also become a powerful clinical trials and basic research tool. Versatile arrays will be useful in developing important analytical arrays.

MATTR technology can be used to detect mRNA in cancer cells to determine which of several important cancer proteins are being produced. Analysis will be performed on cDNA prepared from cellular mRNA by RT-PCR. RT-PCR is a powerful and sensitive method for amplifying specific cellular mRNA (Latchman, 1995) and is becoming a powerful method for both qualitative and quantitative molecular diagnostics (Freeman et al., 1999). In RT-PCR, mRNA is isolated (either total or polyadenylated RNA). RNA is then reverse-transcribed to complementary DNA (cDNA) using the retroviral enzyme, reverse transcriptase ("rt"). Primers (gene specific or universal) are required to initiate reverse transcription. Product cDNA is amplified, as with the polymerase chain reaction ("PCR"), etc., to give detectable quantities of cDNA. RT-PCR is an established method that is often used to detect cancer gene expression (for a review, see Seiden & Sklar, 1996). In almost every published report of RT-PCR analysis of cancer gene expression, only a single type of mRNA has been detected, and detection has been via electrophoresis and detection by radiolabel or stain.

Currently, single tests of individual gene mutations and expression are used clinically in oncology for detection of tumor cells. Someday, vast cDNA microarrays will be commonly used to detect and characterize tumor cells on the level of the whole genome (Schena et al., 1995; Harkin, 2000). In the short term, smaller panels of selective tests will become extremely valuable in the sensitive detection and characterization of tumor cells. Array testing of cancer gene expression will not only provide a more reliable diagnosis, but also will offer a much more informative picture of a patient's prognosis.

Analysis of Nucleic Acids:

MATTR-based nucleic acid analysis will have much in common with immunoassays analysis by the same technology. The major differences are described here. Assays may take place as follows;

(1) A MATTR chip (FIG. 6), with specific capture molecules on its surface, is exposed to analyte solution and the analyte binds to the surface. In one type of assay, the captured analyte is detectable because it itself has been pre-labeled with CL molecules (Schena et al., 1995). The target cDNA can be labeled using any of the many well-known methods and reagents (TriLink BioTechnologies, Inc. San Diego, Calif.; Glen Research Corp., Sterling, Va.). It is preferable to label the target with multiple CL reporter groups. For example, DNA can be chemically biotinylated and the biotin-DNA molecule can bind streptavidin labeled with multiple luminol molecules. Alternatively a sandwich type format can be employed in which a secondary probe is used (Kricka, 1999). In this format, the primary probe, immobilized on the chip, captures the unlabeled target molecule, which in turn captures the CL-labeled secondary probe.

Figure 6:
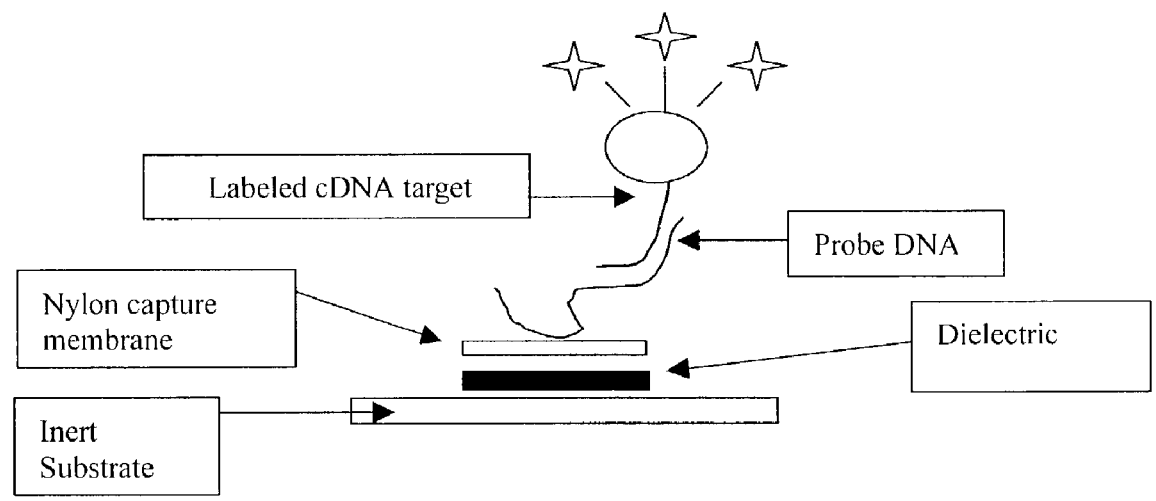
FIG. 6: MATTR-based nucleic acid microarray assay. Upon microwave heating, light emission from multiple CL labels signals the presence of the analyte.

The capture molecule layer is spotted on a nylon membrane (FIG. 6). The nylon may be a full-size overcoat or punched into small circles. The actual spotting process is carried out using a manual microarray spotter (Xenopore Corp.), which can deposit spots on a standard 1"×3" microscope slide. The manual microarrayer is a simple bench top device, measuring only 5"×5" and weighing less than three pounds. It requires no external power source. Uncoated or derivatized glass microscope slides, coverslips, porous membranes, gels, or plastics.

(2) Once binding has been completed, the chip is placed in a chip holder in a MATTR instrument and measurement is made. It should be noted that, as expected, the microwave-generated heat will denature the analyte, but the signal will not be affected.

Description of Analysis of a Specific mRNA

Expression of a specific cancer gene in a tumor cell line can be detected, for example, using a modification of the method of Leitzel et al. (1998) in which RT-PCR was used to detect EGFR mRNA in tumor cell lines. EGFR is a notable prognostic marker in breast cancer.

The appropriate cell line expressing EGFR is cultured (A431 epidermoid carcinoma cells (American Tissue Culture Collection, Manassas, Va.) as well as a control cell line. Appropriate hybridization primers, which could be used on a MATTR chip to demonstrate the detection of EGFR cDNA are disclosed by Leitzel et al. (1998). Total RNA is isolated from cells, and RT-PCR is performed. During RT-PCR, the cDNA is labeled with biotin by established procedures. Biotinylated cDNA is captured on a nylon-coated MATTR chip by specific primer. Luminol-labeled streptavidin is then added, which binds to the captured biotin. Addition of a small amount of peroxide and microwave irradiation results in light emission, which is detected by film or electronic means.

Comparison with Alternative Preparative Technologies

Almost invariably microtiter plate- or microarray chip-based analyses of protein or nucleic acids require preparation of the plates or chips prior to analysis (Price & Newman, 1997; Wild, 2000) involving coating with a specific protein or nucleic acid. Directed microwave heating can be used to accelerate these preparations by targeting heat to proximal dielectrics, which selectively warm the surface of the plates or chips.

Plate surface-directed microwave heating gives superior results when compared to conventional bulk heating in, for example, a 37° C. incubator chamber. The advantage is related to the fact that in a bulk incubator the entire plate and its contents are uniformly warmed while in surface-targeted microwave heating, the plate binding surfaces are preferentially warmed. Surface binding reactions are therefore preferentially accelerated.

There are thousands different types of plate or chip preparative reactions, but typically each involves immobilization of either a binding macromolecule (protein or nucleic acid) or a small molecule ligand. Arrays (libraries) of small molecule ligands such as peptides or other small organic molecules are often synthesized in situ using combinatorial chemistry methods. The technology for macromolecule immobilization and small organic molecule combinatorial chemistry of the present invention is compared to existing technologies below.

It is a distinct advantage of the present invention that surface microwave heating can be used both for preparative reactions and, in the same location, for subsequent analytical reactions. Described below are innovative ways in which preparative and analytical microwave reactions can be used sequentially.

Advantages of the Present Invention in Protein and Nucleic Acid Immobilization:

Prior to immunoassays and DNA probe assays, capture molecules are immobilized on microchips or microtiter plates. Immobilization is often by simple adsorption of the capture molecule to the glass or plastic surface. This procedure usually involves incubation at room temperature for several hours, or at 37° for approximately 2 hours. Elevated temperature heating takes place in a warm chamber (incubator). The present invention discloses two new and improved ways in which molecules can be immobilized. The new ways can be used independently or together. One way is to use microwave heating of the underlying dielectric to gently incubate the surface at approximately 37° C. The other way is to use the piezoelectric properties of underlying ceramic dielectrics to create ultrasonic vibration (sonication), causing the biomolecules to bind to the solid support faster than without sonication. These two methods are described in greater detail below.

(1) Accelerated Immobilization Using Targeted Microwave Heating. Binding of a macromolecule such as a protein or nucleic acid is a surface phenomenon. If the surface is warmed, binding occurs faster. Advantages to microwave surface targeted warming were surprisingly found. By microwaving the binding surface rather than the bulk liquid phase as is normally done, heat is directed to the molecules near the surface. Besides unprecedented capture molecule binding speed, another advantage of using dielectric surface heating is that the same dielectric can be used later for analytical purposes. Protein or DNA capture molecules are bound using microwaves, and then microwaves are used to accelerate a reaction (chemiluminescence, for example) in analyte detection. It has been found that (as is documented in standard protocols) incubating at elevated temperatures such as 37° C. accelerates both non-specific attachment of proteins to surfaces and biospecific (e.g., antibody-antigen) binding on solid phases. Both types of binding can be accelerated by directed microwave surface heating as described herein.

(2) Accelerated Immobilization Using the Piezoelectric Effects of Ceramic Dielectrics To Cause Sonication. The second method of enhancing protein or nucleic acid binding is to exploit the piezoelectric effects of dielectrics, especially ceramic dielectrics. Previously it has been shown that piezoelectric effects cause solution sonication that in turn accelerates biomolecular-surface binding (Sizto & Gallup, 1996; Wohlstadter et al., 2002). The present invention finds that the dielectric can function both to accelerate binding and to accelerate an analytical/preparative chemical reaction (chemiluminescence, for example). Piezoelectric sonication accelerates binding of the molecules to the glass or plastic surface, and also accelerates biomolecule-biomolecule (analyte) binding (capture).

Advantages of the Invention in Solid Phase Combinatorial Chemistry:

Increasingly large libraries of low molecular weight compounds are screened or tested for the ability of proteins or nucleic acids to bind to them. The present invention surprisingly can be used both for synthesis (on chip or plate or other solid support) and for subsequent analysis. First, directed microwave heating is used to accelerated chemical synthesis on the surface, then microwave heating is used in the analysis of the surface (chemiluminescent receptor binding assay or immunoassay, for example. Advantages of small-scale synthesis, followed by analysis include the fact that less waste is generated (an environmentally-sensitive method) and microwave heating on a small scale uses less energy (microwave heating is in general considered a "green technology").

Numerous chemical solid phase libraries are synthesized. For example peptide libraries can be made to search for lead compounds that bind to a protein receptor. Synthesis can occur, with or with our robotics, on the surface in open air, or immersed in an air-tight plastic chamber for air sensitive reactions.

Smaller libraries (2-1000 distinct chemicals) are called focused libraries. Focused libraries of compounds can be made, using microwave surface dielectric heating. The libraries can then be assayed on the same chip using microwave-accelerated reactions to detect binding or catalysis.

Microwave-accelerated chemistry has existed in the literature for almost twenty years and is becoming increasingly popular with organic chemists involved in combinatorial chemistry and drug discovery (Lew et al., 2002; Wathey et al. 2002; Kappe, 2002). To fill the growing demand, at least three companies; Personal Chemistry (Uppsala, Sweden), CEM (Wilson, N.C.), and Milestone (Italy) offer instruments and kits for solution phase reactions. All commercial products involve solution phase syntheses in irradiated tubes. Although not yet significantly commercialized, solid phase, solvent-free microwave chemistry is also becoming increasingly visible in the scientific literature (Wathey et al., 2002). Microwave chemistry often reduces reaction times by 10-fold or more, while increasing yields substantially (Table 4).

TABLE 4

Examples of Microwave-Assisted Organic Chemistry

| Reaction Type | Conventional time/yield | Microwave time/yield | Reference |
|---|---|---|---|
| Peptide synthesis | 30 min/70.5-94.8% | >6 min/99.5-100.0% | Yu et al., 1992 |
| Claisen rearrangement | 10-16 hr/84-92% | 4-6 min/84-92% | Lew et al., 2002 |
| Solid-supported Lawesson's reagent equivalent | 30-40 hr/>95% | 15 min/>96% | Wathey et al., 2002 |

On-chip dielectric-directed microwave combinatorial chemistry (MATTR) has not been reported until now. In MATTR, the reaction mixture is indirectly targeted by microwaves—the dielectric chip is the targeted and heat transfer to the proximal reactants drives the reactions. Evaporation is minimized by an inert PTFE chip cover, if necessary. In essence, MATTR for the first time unites the fields of microarrays, combinatorial chemistry, and microwave chemistry.

Until now, on-chip synthesis has been unattractive because in many cases the size of the effort was not worth the information gained in an experiment. Conventional (long) reaction times were necessary to prepare chips that would be used only once or twice, and then discarded. MATTR will drastically reduce the synthesis time so that synthesis and analysis can be done in a single day. Moreover, MATTR is a low-solvent volume chemistry that generates little waste. Having now generally described the invention, the same will be more readily understood through reference to the following examples, which are provided by way of illustration, and are not intended to be limiting of the present invention, unless specified.

EXAMPLES

Example 1

Microwaves Preferentially Directed to Carbon Particles Suspended in Water

An experiment was carried out to test whether carbon particles in water would heat substantially faster than the water they are suspended in. The experiment involved a conventional kitchen microwave oven (Panasonic NN-S949, 1100 W output, 2.45 GHZ). Carbon is known to be lossier than water at the emitting frequency. Thus, a suspension of carbon (approx. 200 mg) in water (approx. 100 mL) should heat faster than neat water. Water (100 mL) was heated in the absence or presence of ground carbon (charcoal briquettes (Super G, Landover, Md.) were ground to a powder using a mortar and pestle). After 1.0 minute of microwaving, the carbon-containing water was nine degrees warmer (83° F.) than water alone (74° F.). (The heated carbon transferred its heat to water, which I measured). The experiment was repeated and similar results (nine degrees hotter in the presence of carbon) were found. This shows that substances can be preferentially heated in water by dielectric heating. Alternatively, a different dielectric material could have been used which heated much faster than carbon at 2.45 GHz, or a different frequency could be used which does not heat water well, or both.

Example 2

Microwaves Preferentially Directed to Hydrated Clay

Three experiments were carried out to test whether hydrated clay would heat substantially faster than the water. A report by Buffler & Risman (1996) indicated that clay would heat faster than water, especially at 915 MHz. Clay is moldable and could be used as a core dielectric in beads or as a flat surface in cartridges. To test this hypothesis, a 2450 MHz emitting microwave oven was employed. Based on the report of Buffler & Risman, any positive result in these (2450 MHz) experiments would indicate that much better results could be obtained at 915 MHz.

Experiment 1: Approximately 100 mL spring water were heated in a plastic microwavable cup for 60 seconds in the same microwave as described in Example 1. The temperature rose from 25.0° C. to 92.5° C. The same volume of water, but containing approximately 200 mg clay (Bentonite 200 clay, supplied as dry powder from Great Lakes Clay and Supply Co., Carpentersville, Ill.) was also heated in the microwave. The temperature rose from 25.0° C. to 94.5° C. This experiment indicated that clay heated more than water and the temperature change in the presence of clay was due to (minor) heat transfer from the (hot) clay particles to the bulk water.

Experiment 2: Approximately 200 mL spring water was heated in a plastic microwavable cup for 45 seconds in the same microwave. The temperature rose from 19.0° C. to 49.0° C. The same volume of water, but containing approximately 50 mg clay (Bentonite 200 clay) was also heated in the microwave. The temperature rose from 19.0° C. to 52.0° C. This experiment provided verification that clay heated more than water and the temperature change in the presence of clay was due to (minor) heat transfer from the (hot) clay particles to the bulk water.

Experiment 3: Approximately 50 mL room temperature spring water was heated in a plastic microwavable cup for 30 seconds in the same microwave. The temperature rose to 68.0° C. The same volume of room temperature hydrated Bentonite 200 clay (minimal liquid water) was also heated in the microwave. The temperature rose to 84.0° C. This experiment verifies that clay heats faster than water when exposed to 2450 MHz (1100 W) microwave irradiation. It also indicates that the increase in temperature of the clay-containing water in Experiments 1 and 2 was due to (minor) heat transfer form the substantially hotter clay to the cooler water. Microwave heating was directed to clay in the presence of water.

Example 3

Preparation of Carbon-Containing Molecular Imprinted Polymer Particles that Bind L-Phenylalanine-p-Nitroanilide There are many possible physical formats in which an artificial biomolecule is in thermal proximity to the microwave-heated dielectric. One type of format is a bead or particle. In the embodiment described here, carbon particles (the dielectric) and molecularly imprinted polymer (the artificial biomolecule) are formed into composite particles.

The polymer is created from monomers and crosslinkers in a solution containing both the print (template) molecule. Also present in suspension are carbon particles. As polymerization occurs, the growing crosslinked polymer entraps both the template molecule and the carbon particles.

The polymer/carbon particle composite is ground to small fragments. This, the carbon particles and imprinted binding sites in the polymer are present in close proximity.

This example describes in detail the preparation of such a dielectric/artificial biomolecule composite material. The composite can be used to selectively hydrolyze L-phenylalanine-p-nitroanilide from a mixture of L- and D-enantiomers.

Synthesis of D- and L-phenylalanine-p nitroanilide (O'Shannessy et al., 1989a). The D- and L-phenylalanine anilides are synthesized by coupling the corresponding BOC-derivatives with aniline using 1,3-dicyclohexylcarbodiimide/1-hydroxybenzotriazole as condensation agents in N,N-dimethylformamide. After deprotection with trifluoroacetic acid, the resulting solid is solubilized with 0.1 M HCl, filtered, and extracted with toluene. The pH of the aqueous phase is adjusted to 9 by addition of 1 M NaOH and the free bases of the anilides were extracted into ethyl acetate. The free bases of the anilides are then crystallized from 1-propanol/hexane.

Preparation of carbon particles. Small carbon particles can be prepared from charcoal as described in Example 1 above. Alternatively, activated carbon (Darco® KB, 100 mesh, Aldrich Chemical Co., Milwaukee, Wis.) can be used. In either case, the carbon is ground using a mortar and pestle to create fine particles. The carbon particles are suspended in chloroform and sieved through a 10 µm sieve. The chloroform that passes through the sieve is evaporated down until a fairly concentrated suspension of carbon particles is obtained. This carbon suspension will be used as the solvent during molecular imprinting polymerization.

Preparation of molecularly imprinted polymer/carbon composites (O'Shannessy et al., 1989a; O'Shannessy et al., 1989b). The carbon particle-containing chloroform described above is used as the solvent. Into a glass 50 mL tube is added; 1.956 mmol of the print molecule L-phenylalanine-p-nitroanilide (PPNA), 7.86 mmol of the functional monomer methacrylic acid (MMA), 39.3 mmol of the crosslinker ethylene glycol dimethacrylate (EDMA), 12 mL of the solvent, and 0.57 mmol of the initiator 2,2'-azobis(2-methylpropionitrile (AIBN). The tube is sealed and full solubilization is achieved by sonication. The mixture is degassed by sonication and sparged with nitrogen for 5 minutes. The mixture is cooled to 4° C. At that temperature, the mixture is illuminated overnight using a standard laboratory UV source (366 nm) with very gentle agitation to prevent the suspended carbon particles form settling.

The formed polymer (solid) is broken into small pea-sized pieces, then ground to a powder using a mortar and pestle. The powder is suspended in chloroform, then filtered through a 100 µm sieve. Using a sintered glass funnel, the print molecule is removed by solvent exchanges. A 30:70 mixture of ammonium hydroxide ($NH_4OH$) and acetonitrile ($CH_3CN$) is used followed by $CH_3CN$ alone. Finally, the composite particles are dried.

Example 4

Microwave Hydrolysis of L-Phenylalanine-p-Nitroanilide; Molecularly Imprinted Polymer Dielectric Particles in Contact with the Reactant Solution Hydrolysis of L-phenylalanine-p-nitroanilide (L-PPNA) is carried out in the presence of the imprinted composite particles described in Example 3. The particles (0.2 g) are suspended in a 50 mL solution (0.1 mM) of L-PPNA. The L-PPNA solvent is 80% $CH_3CN$/20% $H_2O$ (water is neutral pH).

The particle/substrate solution is placed in a 1100 W/2.450 GHz microwave. Microwaves are generated for a time sufficient to accelerate the reaction at the surface of the particles. As controls, the same experiments (microwaving L-PPNA solutions) are repeated in the absence of particles.

Analysis of the quantity of p-nitroaniline is carried out, either by spectrophotometric or HPLC analysis (both types of analyses are know to those skilled in the art). Results show that more p-nitroaniline is generated in the presence of particles.

To show that microwave hydrolysis is not a result of non-specific binding of L-PPNA to the particles, the experiments are repeated with D-PPNA. The results show that, under identical conditions, more L-PPNA is hydrolyzed than D-PPNA. These results show that the hydrolytic binding sites have enantiomeric specificity for L-PPNA.

Catalytic molecularly imprinted polymers (artificial enzymes) have been described previously (Leonhardt and Mosbach, 1987; Bystrom et al., 1993), but this is the first description of an artificial enzyme in which catalysis is accelerated through directed heating by microwaves.

Example 5

Microwave Hydrolysis of L-Phenylalanine-p-Nitroanilide; Molecularly Imprinted Polymer Dielectric Particles in Contact with Air Hydrolysis of L-phenylalanine-p-nitroanilide (L-PPNA) is carried out in the presence of the imprinted composite particles described in Example 3. The particles (0.2 g) are suspended in a 50 mL solution (0.1 mM) of L-PPNA. The L-PPNA solvent is 80% $CH_3CN$/20% $H_2O$ (water is neutral pH).

Following sufficient time for L-PPNA to reaching binding equilibrium with the molecularly imprinted polymers, the composite particles are filtered from the reactant solution and briefly washed with water to remove excess reactant.

The filtered particles are placed in a 1100 W/2.450 GHz microwave oven. Microwaves are generated for a time sufficient to accelerate the reaction at the surface of the particles. As controls, the same experiments (microwaving L-PPNA solutions) are repeated in the absence of particles.

Analysis of the quantity of p-nitroaniline is carried out, either by spectrophotometric or HPLC analysis (both types of analyses are know to those skilled in the art). Results show that more p-nitroaniline is generated in the presence of imprinted particles than control (non-imprinted) particles.

To show that microwave hydrolysis is not a result of non-specific binding of L-PPNA to the particles, the experiments are repeated with D-PPNA. The results show that, under identical conditions, more L-PPNA is hydrolyzed than D-PPNA. These results show that the hydrolytic binding sites have enantiomeric specificity for L-PPNA.

Example 6

Preparation of a Zeolite-Coated Clay Dielectric Surface

Zeolites are porous inorganic solids used to catalyze specific chemical reactions in many applications, including the conversion of crude oil to gasoline and the in automotive mufflers to remove CO, NOx, and hydrocarbons from gaseous exhaust (Rouhi, 2000). The reactions take place within confined cavities inside the zeolites. As with any chemical reaction, reaction rates within the spaces of zeolites increase with temperature.

Zeolites can be immobilized on porous and non-porous solid surfaces (van Bekkum et al., 1994; Jansen et al., 1994), including the surfaces of dielectric microwave-responsive materials. Coatings of zeolites can be either films or layers. A film is a continuous solid phase of microporous crystals oriented in a parallel mode on a support. A layer is a (dis)continous solid phase of microporous crystals more or less disorderly oriented on a support. The preparation of zeolite coatings is well known (Jansen et al., 1994). The coatings can be formed by application of the formed zeolites, or by growing the zeolites on the surface.

In this example, Y zeolites (Zeolyst International, Valley Forge, Pa.) are affixed to an approximately 0.5 cm×0.5 cm surface of Bentonite 200 clay by the technique of dip coating. (Alternatively, other dielectric materials such as carbon could be used as the support.) Dip-coating is an efficient and well-proven method to apply zeolites to surfaces and may be used with most support surfaces (van Bekkum et al., 1994). The Y zeolites are made into a slurry containing a dissolved polymeric substance, which forms the continous phase layer after solvent removal. The binder, which is commonly added, which upon curing assists in the formation of a strongly bonded zeolite layer on the surface.

Example 7

Microwave-Accelerated Homolytic Cleavage of 1-Naphthyl Phenylacetate on a Zeolite Y-Coated Clay Dielectric Surface A Zeolite Y-coated clay chip (Example 6) is placed in the bottom of a 50 mL beaker. Hexane (20 mL) containing 1-naphthyl phenylacetate (NP)(10 mM) is added (Gu et al., 1999). The beaker is placed in a microwave oven (Panasonic NN-S949, 1100 W output, 2.45 GHZ) and microwaves are generated until the reaction occurs on the zeolite surface. Following irradiation, the bulk hexane solution is characterized by gas chromatography as described (Gu et al., 1999). The surface zeolites are extracted into pure hexane and the extract is also characterized by GC. The extent of the reaction of NP is greater in the zeolite extract than in the bulk hexane solution (there is a higher product-to-reactant concentration ratio).

In a second experiment, two zeolite-coated clay chips are immersed in separate beakers containing 10 mM NP in hexane. One beaker is exposed to microwave irradiation, while the other beaker is not. The zeolite-clay chips are extracted into hexane, and analyzed by GC. The microwave-irradiated zeolite will contain a higher product-to-reactant ratio than the non-micro waved zeolite.

Example 8

Coating a Dielectric Molecular Imprinted Polymer with an Insulating Mesoporous Silica Layer In some cases it might be necessary to further encapsulate the dielectric/artificial enzyme composite. A porous thermally insulating capsule or layer would reduce heat transfer from the dielectric to the bulk solvent. (It is also noted above, that an equivalent result could be obtained by cooling the bulk solution using a cooled container.)

A number of materials, primarily polymers, could be used as the insulating layer. The requirements of such materials are that it must reduce heat transfer while also, at least minimally, allowing reactants to pass through. The thickness of the porous layer can be optimized depending on various factors including the reaction to be catalyzed, the types of materials used, and the specific application desired.

In the case of a molecularly imprinted polymer, one technique is to coat the surface of the imprinted polymer with the same polymer, minus the print molecule. Thus, the order of materials would be dielectric/imprinted polymer/non-imprinted polymer/bulk solution. As referenced above, forming layers of polymers is known in the art.

The present example describes how a porous silica layer can be used to coat and insulate an dielectric/artificial enzyme composite. A dielectric surface coated with a layer of molecularly imprinted polymer is coated with silica. To coat an imprinted polymer with a silica layer, a stock solution is first prepared (Makote et al., 1998). The solution contains tetramethoxysilane (TMOS), phenyltrimethoxysilane (PTMOS), ethoxy ethanol (EE), water, and 0.1 M hydrochloric acid. The ratio of TMOS to PTMOS is 10:1. The pH of the solution is raised to 7 using potassium hydroxide. After 30 minutes, the solution is coated on the dielectric/molecularly-imprinted polymer. The coating method can be by using a spin-coater (Makote et al., 1998), or spraying, or dip coating. The resultant coated surface is allowed to dry in a dessicator at room temperature. To further enhance the insulating properties of the silica coat, the coating process can be repeated multiple times to form multiple layers.

Example 9

Film-Based Detection of Microwave-Accelerated Chemiluminescence

A number of experiments were carried out to test the invention using chemiluminescence reactions. In the experiments, microscope slides were prepared as "chips" on which luminol/peroxide reactions took place to give light. The chips were either plain (glass) or had a dielectric. Dielectrics used were barium titanate or activated charcoal. Film was used to detect light from the CL reactions, with and without microwave irradiation.

Experimental:

Chips: Dielectric chips were made from standard microscope slides (1 inch×3 inch×1 mm) (VWR Micro Slides). Two types of chips were made. One type was made by spotting dielectric slurries onto microscope slides. Spots were approximately 0.5 cm in diameter. The CL reaction was then run directly on top of (in contact with) the dielectric. The other type of chip was a sandwich of two microscope slides with nothing (control chips) or a contiguous film of dielectric between the slides. With the "sandwich chips", the CL reaction was run on the upper glass slide, not in contact with the dielectric layer. The dielectrics used were barium titanate (Aldrich Chemical Co., 20,810-8) and activated charcoal (Sigma Chem. Co. C4386). Thick slurries of dielectrics were prepared by mixing with water. Barium titanate formed a thick paste and charcoal formed a less dense mixture.

Chemiluminescent Reactions: Luminol (3-aminophthalhydrazide monosodium salt, Alfa Aesar 44007) reacts with hydrogen peroxide at alkaline pH. Solutions of luminol were prepared at various pH values from approximately 7.9-10.2. The solutions also contained copper(II)sulfate pentahydrate and buffer (sodium bicarbonate). Various concentrations and pH values were tried, but it was finally determined to use pH 8.0 and a luminol concentration of luminol was 4.4 mM (stock solution, which was mixed 1:1 with the peroxide solution to initiate the reaction). At higher pH values the reaction went too fast and was apparently more than halfway completed in the first minute. The lower pH caused the reaction to proceed much more slowly. Lower luminol concentrations were feasible but 4.4 mM was desired to obtain bright spots on film.

The luminol solution was mixed with an equal volume of dilute hydrogen peroxide to begin the CL reaction. Hydrogen peroxide, 3%, was diluted 1:20. This was the stock solution (0.15%).

On chips, the total volume of the spots was either 6.0 μL (3.0 of each luminol and peroxide) or 3.0 μL (1.5 of each).

Data Recording: To be most sensitive, the technology will use CCD or PMT detection and analysis of CL light. Alternatively, it is convenient to use film, especially in cases where quantitation is not critical, but a qualitative measure of some signal is needed. Additionally, a film-based system may be attractive where disposables are needed, rather than say, a CCD camera.

Data was recorded on sheets of Amersham Hyper ECL film and developed according to conventional methods. In all cases, under microwave irradiation or not, film was exposed to CL chips for 20 seconds. Film development was through conventional means (Kodak D-19 developer).

Chip Holder: A chip holder was made from a music CD case. The clear methyl methacrylic case acted as a thermal insulator to prevent the film from getting hot. It also prevented the film from contacting the reaction surface. The CD case had within it a cardboard insert to prevent chips from moving. The edges of the film were taped lightly to the outside of the CD box over the chips, and the CD box was placed in a light-tight cardboard box. The box was then placed in a microwave oven (see Example 1 for description of the oven).

Experiments Performed and Results: In all cases, chips were used once and discarded. Microwaving was performed on a rotating tray to reduce uneven heating. No evidence of artifacts due to uneven heating was observed (multiple experiments gave results that were in agreement with each other).

1) Spotted Chips. Initial work with spotted chips gave equivocal results. This is believed due to the fact that the reagents were spotted directly onto the dielectric material. The reactants may have soaked into the dielectric layer somewhat or spread unevenly. It was difficult to determine the success or failure of the experiments using both carbon and barium titanate dielectric layers for this reason. It should be noted that direct contact of the dielectric and the binding reagents is not a requirement of the invention (see FIG. 2C).

Figure 7:
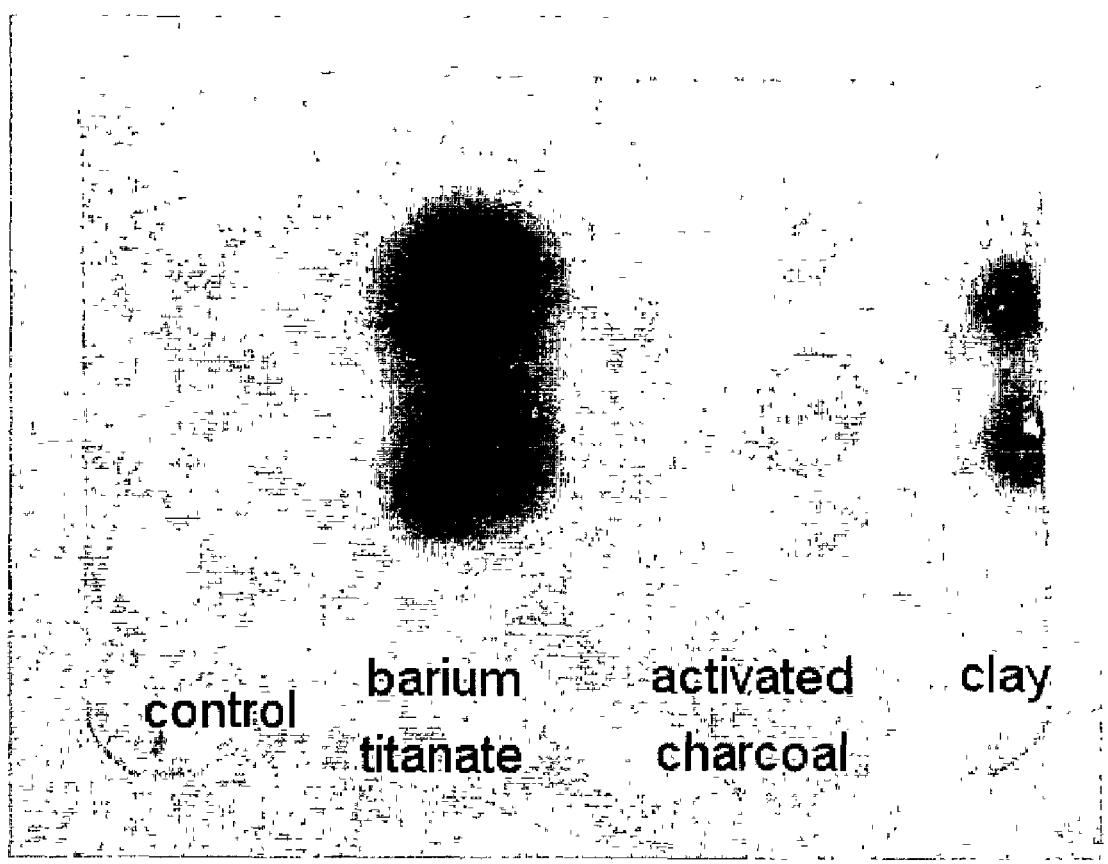
FIG. 7: Demonstration of Microwave-Accelerated Triggered Chemiluminescent Reactions. This figure demonstrates that, compared with "blank" glass microscope slide-based (labeled Control), dielectric chips containing barium titanate, activated carbon, or Bentonite clay substantially accelerate the chemiluminescent reaction of luminol/peroxide under microwave irradiation.

2) Sandwich Chips. Results with so-called sandwich chips were much better than with spotted chips. As stated above, sandwich chips comprise three layers; a microscope slide, a middle dielectric layer, and another microscope slide. These chips have two major advantages over spotted chips used above. One is that the reaction occurs on glass (a known surface) rather than on an uneven dielectric spot. The second advantage is that the dielectric layer is large, covering the entire 1×3 inch surface of a slide. This larger amount of dielectric means that the chip can be hotter. (It should be noted that the surface of sandwich chips can be partitioned into hot and cold zones by adding additional non-contiguous layers.)

a) In one experiment 3 μL of luminol stock solution was mixed with 3 μL of peroxide stock solution. There were 2 spots on each of three chips, glass (no dielectric), barium titanate, and activated charcoal. The chips were placed side-by-side in a chip holder and film taped to the holder. The chips were microwave-heated for 20 seconds and the film was developed. The developed film revealed that there was some light emitted from the glass chip (two spots could be seen) but much more light emitted from the barium titanate spots and the charcoal spots. Indeed, the charcoal chip gave a huge amount of light that was scattered, suggesting that the heat (20 seconds) was so intense that the reagent spots sprayed. Upon opening the chip holder following microwaving, the chips were all visible intact and the dielectric chips were dramatically hotter to the touch than the control chip.

b) In a second experiment, the experiment described in a) was repeated. Essentially the same results were obtained.

c) In a third experiment, three chips were again spotted, this time with 1.5 μL each of luminol and peroxide per assay (half the amount used above). It was observed by eye that luminescence a room temperature glowed steadily for several minutes. For this reason, the chips were first assayed at room temperature (20 seconds exposure to film), then placed in the microwave with new film and exposed for another 20 seconds during microwaving. After developing, the two films were compared. The film exposed to chips (20 sec.) prior to microwaving showed light spots corresponding to the CL reactions on all three ships. (Although all were fairly faint, the barium titanate chips consistently gives darker spots in control experiments, suggesting that the white color of the dielectric reflects light upward to the film.) The film exposed to slides during microwaving looked very different. The glass (no dielectric) chip showed no difference from the room temperature exposure—the spots were light. However, the film captured dramatically more light over the dielectric chips. The barium titanate chip gave darker spots that in the control (room temperature) experiment. As seen previously, the image of the activated charcoal spots was very intense and scattered, suggesting that a very large amount of light was emitted and the temperature may have been very high. This experiment demonstrates, as above, that microwave heating accelerates CL reactions on a dielectric chip.

d) The experiment described in c) was repeated with virtually identical results. The room temperature spots were faint, but the microwave spots (with the exception of the control spots) gave dark images on film. These data clearly demonstrate reduction to practice of microwave targeted accelerated reactions.

e) An experiment was performed to verify that the dark spots seen on film were indeed from the CL reactions and not an artifact of the chips themselves. Four chips were prepared; control (two glass microscope slides), barium titanate, activated charcoal, and another dielectric chip, containing Bentonite clay (prepared from powder with deionized water). No CL reagents were placed on the chips. The four chips were placed in the chip holder, X-ray film was attached and the holder was microwaved for 20 seconds. The developed film was completely blank, indicating that all the darkness on films seen originated from CL light emission.

f) The experiment described in c) and d) was repeated except for two variations. One change was that less activated charcoal was used in the chip. The other change was that four chips instead of three were used—a Bentonite clay dielectric chip was added. FIG. 7 shows the results. Each vertical lane is the image from one microscope slide-based chip. On the film can be seen two faint spots in the Control lane. These represent CL emission from two assay spots on the glass-only chip. The other chips show stronger light emission; barium titanate spots, activated charcoal, and Bentonite clay. All of these substances can be used to accelerate chemical reactions on a chip.

Example 10

MATTR Signal Amplification Using Glucose Oxidase-Generated Hydrogen Peroxide

In some cases it is advantageous or necessary to use an enzyme to amplify the signal in a nucleic acid assay or immunoassay. This is often done with conventional nucleic acid assays and immunoassays (Enzyme-Linked Immunosorbent Assays or ELISAs). Enzyme-generated signals can be calorimetric, fluorescent, or chemiluminescent. Briefly, in ELISAs the analyte is captured on an immunospecific solid phase. Biospecific analyte binding can be in competition with the analyte labeled with signal generating enzyme (a competitive assay). Alternatively, a secondary antibody labeled with signal generating enzyme can be used (a sandwich assay). In both cases, bound enzyme catalytically transforms a substrate to product resulting in a signal change. Amplification of the signal is derived from the fact that each enzyme (label) molecule turns over many substrate (signal) molecules.

Microwave induced ELISA signal generation has not been reported until now. In a microwave-induced ELISA, the enzyme catalyzes a reaction that changes physicochemical properties of one or more molecules, but little or no signal change occurs until the sample is microwave heated. Signal change (chemiluminescence, etc.) occurs upon microwave irradiation.

To test microwave induced ELISA, an experiment was performed with the glucose oxidase (GOx) from A. niger (Sigma G-9010) as the label enzyme. GOx is often used as the signal-generating enzyme in ELISAs. It catalyzes the oxidation of glucose to produce hydrogen peroxide, which can participate in calorimetric or luminescent reactions. This system is ideal for microwave-induced luminol-peroxide chemiluminescence. Glucose oxidase functions most efficiently at pH 5.0-7.0, while luminol-peroxide reacts fastest at pH 9.0-11.0. Thus, the enzyme reaction is first allowed to proceed efficiently at pH 7.0 to generate peroxide. At this neutral pH, peroxide will not appreciably react with luminol until microwave irradiation occurs. Irradiation will heat the reaction, vastly accelerate its rate, and cause immediate chemiluminescence.

Reagents: (a) glucose oxidase (2.0 units/1.5 µL), (b) glucose (10 mM/1.5 µL), (c) luminol/$CuSO_4$ stock of 0.2 g/L and 0.4 g/L, respectively, was diluted with 250 mM $NaHCO_3$ to a luminol concentration of 18 µM/1.5 µL.

Dielectric Chip: a barium titanate sandwich chip was used (aqueous paste between two microscope slides).

Instrumentation/Detection: Microwave oven and X-ray film detection were as described in Example 9.

Experiment 1: Reaction of glucose and GOx (volumes listed above) were carried out on-chip for 2 minutes. Also, control spots of glucose only and GOx only were incubated. Luminol was added to the spots, and the chip was microwaved for 15 seconds. No spots were seen on the X-ray film.

Experiment 2: The experiment was repeated but the reactions were allowed to go for 15 minutes. This time, the GOx/glucose spot gave a dark spot on the film but the two control spots gave no detectable light. Previous control experiments (Example 9) showed little or no light emission without microwave heating under similar conditions.

This experiment showed that a microwave induced chemiluminescence signal can be amplified by an enzyme. It also demonstrated that biochemicals (GOx and glucose) can be detected using this system. It also showed that non-compatible reactions (GOx optimal at acidic pH and luminol/peroxide optimal at alkaline pH) can work together in this system since microwave heating can accelerate a reaction.

Example 11

Use of Directed Microwave Heating to Accelerate Avidin Coating of a Microtiter Plate Experiments were performed to test whether microwaving a dielectric coated plate can enhance the binding of a protein to microtiter plate wells.

Materials and Methods:
Plates: "Dielectric Plates" were prepared as follows. The undersides of Nunc MaxiSorp 96-well flat-bottom microtiter plates (strip well format) were hand painted with a dielectric paste. The paste was made by mixing Barium titanate powder with polyvinyl acetate-based glue (Elmer's Glue-All). The paste was allowed to dry before the plates were used.

Reagents: ImmunoPure Avidin (Pierce Prod.# 21121), Biotinylated Horseradish Peroxidase (HRP-Biotin)(Pierce Prod.# 29139).

Microwave Oven: GE Model JE635, 600W
Spectrophotometer: Tecan SLT plate reader
Experiments and Results:
Experiment 1) The effect of microwaving microtiter plates on avidin coating was tested. Three types of plate treatments were performed; (1) control—no heating, painted plates, (2) control—heated, unpainted plates, and (3) heated, painted plates. Plate wells to be heated (plate treatments 2 and 3) were pre-heated by microwaving for 1.0 min (defrost cycle, 60W). Coating solution (100 µL of avidin (10 µg/mL) in carbonate buffer, pH 8.5) was added to all three types of plates. Plate wells to be heated (2 and 3) were then heated again in the same manner. The plates were allowed to stand for 5 minutes and then rinsed once with PBS. A blocking agent, BSA (250 µL of 0.1 mg/mL), was added and the plates were stored overnight at 4° C. The plates were then washed four times with PBS. HRP-biotin (100 µL, diluted 10,000:1) was added to each well and the plate was incubated 20 minutes. The plates were then washed four times with PBS/Tween (0.05%) and once with PBS only. TMB substrate (100 µL) was added to each well, incubated for 60 seconds, and then 1 M $H_2SO_4$ (100 µL) was added. Absorbance was read at 450 nm.

The results showed mean absorbances of 1.243 (n=8) for Control 1 (no heating, painted), 0.610 (n=8) for Control 2 (heated, not painted), and 2.482 (n=8) for the experimental wells (heated, painted). These data show that the experiment worked, painted plates showed more avidin binding than control plates. It also showed that the bound avidin retained biological activity (ability to bind biotin). It also showed that this method can be used to prepare plates for bioanalysis. The results demonstrated that some minor experimentation is required to optimize the amount of reagents used, as a high degree of binding was seen in all cases (the amount of avidin used was probably excessive). Experiment 2) A second experiment was performed to optimize and verify the results of the first. Avidin was diluted with carbonate buffer to a concentration of 5 µg/mL (100 µL was used per well, or 5 µg). The following sets of wells were used in the experiment; Experimental (heated, painted, 5 min avidin incubation), Control 1 (heated, unpainted, 5 min avidin incubation), Control 2 (not heated, unpainted, 5 min avidin incubation), Control 3 (not heated, unpainted, 30 min avidin incubation). Unless otherwise noted above, the following heat treatments were carried out; wells received 1 min of microwave irradiation (full instrument power), avidin was then added (100 µL), the wells were then irradiated for 20 sec (10 sec on/20 sec off/10 sec on/20 sec off), then incubated for 5 minutes at room temperature (30 min for Control 3). The wells of all plates were rinsed with PBS, then 0.1 mg/ml BSA was added and allowed to block the wells overnight at 4° C. Wells were assayed for their ability to bind HRP-biotin as described in Experiment 1).

Figure 8:
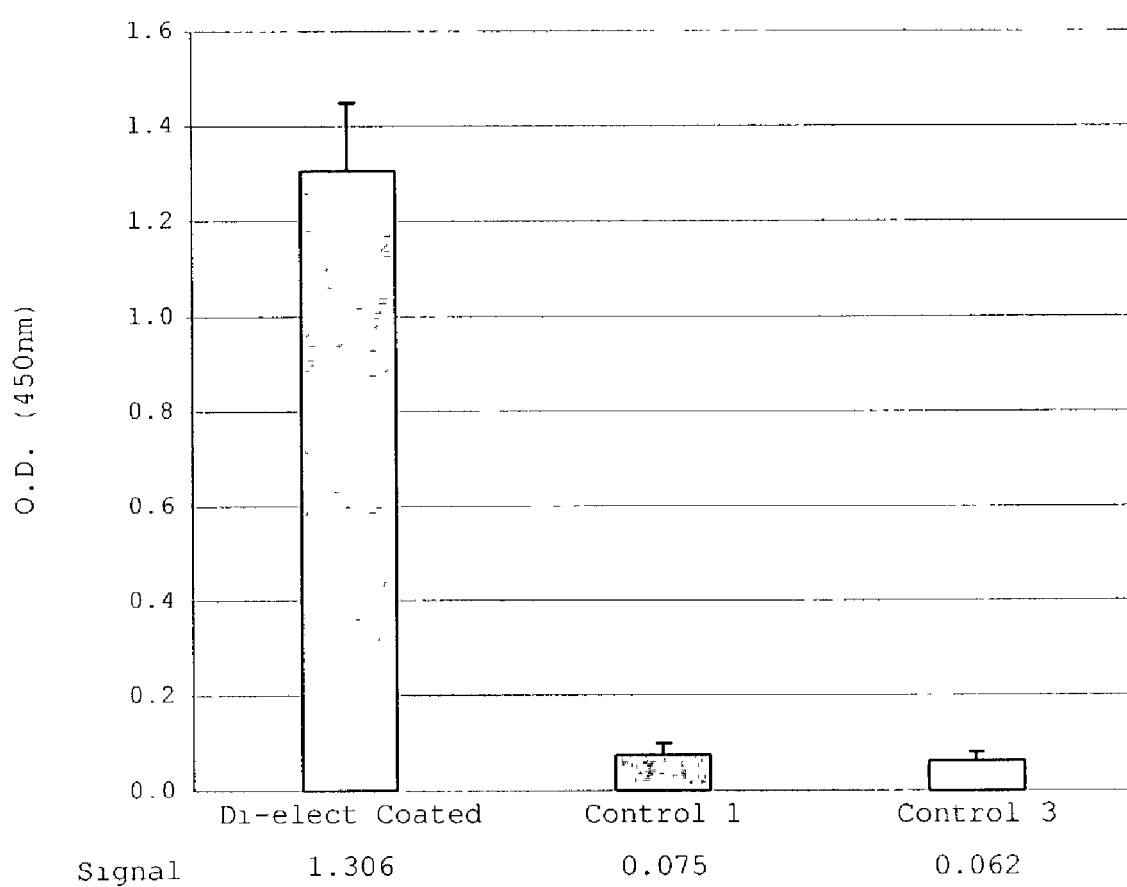
FIG. 8: Effect of MATTR-based protein binding to a microtiter plate.

The results of the Experimental data and two Controls are shown in FIG. 8. Control 2 is not shown because the data were thought to be unreliable (the reading was 0.539). These results confirm the findings of Experiment 1) and show great progress with only one attempt at optimization. The use of dielectric painted plates clearly improves avidin binding to microtiter plates.

Example 12

Synthesis of a c-Myc Peptide on a Dielectric Array Chip

Microwave heating can accelerate the preparation of dielectric chips or microtiter plates by speeding the synthesis of compounds on the surface. Solid phase microwave chemistry is a well-known field. However, a distinguishing feature here is that the solid phase is used as a scaffold on which molecules are built. Another distinguishing feature here is that the finished chemically modified surface is used for biomolecular analysis that involves a biospecific binding event.

Figure 9:
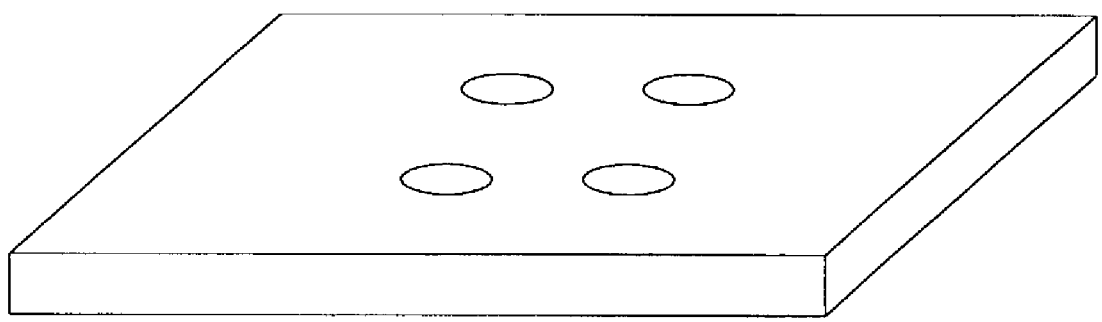
FIG. 9: C-myc derived peptide array (2×2) synthesized on a MATTR chip. Directed microwave heating is used to accelerate on-chip reactions.

Two dielectric chips are made prior to solid phase peptide synthesis. First, an aqueous paste of barium titanate is sandwiched between two standard glass microscope slides and the edges are sealed to enclose the barium titanate. On the surface of this "sandwich dielectric chip" is glued (around the edges) a cut-to-fit piece of cellulosic "SPOTS" membrane (Sigma-Genosys). The cellulose membrane has four acceptor spots for peptide synthesis. Two spots are for the c-myc peptide and two are control spots for a non-c-myc peptide. Thus, two identical chips are prepared—one called the "microwave" chip and the other called the "non-microwave" chip. Both chips contain four spots—duplicate spots for the c-myc peptide and duplicate spots for the non-c-myc peptide (FIG. 9).

Microwaved chip: Using a SPOTs kit (Sigma-Genosys), two peptides are synthesized on the spots. One peptide is EQKLISEEDL (SEQ ID NO: 1), which is derived from the c-myc protein (p62$^{c\text{-}myc}$ proto-oncoprotein) (Hilpert et al., 2001). The other, a control peptide, is the same peptide, but with a histidine for leucine substitution at the fourth residue of the peptide (i.e., EQKHISEEDL (SEQ. ID. NO.:2)). Hilpert et al. showed that leucine is essential in that position for mouse antibody 9E10 to bind strongly to the c-myc peptide. Synthesis procedure is as described (Hilpert et al., 2001 and references cited therein, and Sigma-Genosys technical notes) with the exception that reaction times are shorted where appropriate by a factor of 2 to 20-fold and the shortened reactions are carried out under irradiation by microwaves in a microwave oven.

Non-Microwaved chip: The procedure of the microwaved chip is repeated except that no microwave irradiation is applied to the chip (reaction times are reduced from literature values).

Determination of Success: Success is measured in three ways. First, coupling yields are determined by acid hydrolysis, solution phase ninhydrin staining, and visible spectroscopy. Second, quantitative amino acid analyses are performed on the peptides analysis. Finally, immunoassays of the synthesized peptides are performed as described below in Example 13.

Example 13

Assay of an Anti-c-Myc Peptide Using a Labeled Antibody on a Peptide Library Dielectric Chip The two peptide-modified dielectric chips, "microwaved" and "non-microwaved", prepared in Example 12 are assayed to determine if antibody 9E10 will bind to the c-myc peptide, but not to the substituted peptide. MATTR technology is used to assay the chips. The assay procedure involves anti-c-myc mouse monoclonal antibody 9E10 (Research Diagnostics, Inc, Flanders, N.J.). Antibody 9E10 is incubated with the spots. Following binding and washing to remove excess antibody, the spots are incubated with glucose-oxidase-labeled goat anti-mouse antibody (TCN, catalog #55571). Following washing to remove unbound antibody, bound glucose oxidase is detected using glucose to produce peroxide, which is then detected using luminol at neutral pH. Signal is generated by microwave heating and visualized by X-ray film as described above.

The results from the "microwaved" chip show that light is mainly emitted from the location of the c-myc peptide, rather than from the substituted peptide. This shows that microwave synthesis is successful and that the prepared peptide can be detected in an immunoassay. Further, the results show that microwaves can be used to assemble a chemical compound library on a chip and the library can also be screened using microwave luminescence technology.

The results from the "non-microwaved" chip showed that without microwave heating the synthesis procedure was not as successful as with microwave heating. Less light was emitted from the c-myc spot on this chip than on the "microwaved" chip.

Example 14

Accelerated Biomolecular Binding Using the Piezoelectric Properties of Microwave-Susceptible Dielectrics Fortuitously, some dielectric materials that couple well to microwaves to generate heat also have piezoelectric properties. For example, ceramics such as those that contain barium titanate are both microwave heatable and piezoelectric. This mean that a dielectric component of a microarray chip or microtiter plate or MATTR microwave generating instrument can be used, not only to generate heat to trigger a chemical reaction, but also to vibrate under applied voltage. It has been shown that piezoelectric vibrations (sonication or ultrasonication) can be used to accelerated the rate of biomolecular reactions, especially binding reactions, for example between a ligand and its receptor (Sizto & Gallup, U.S. Pat. No. 4,575,485; Wohlstadter et al. U.S. Pat. No. 6,413,783).

A ceramic dielectric-containing plate or chip can have leads to allow current to pass through the dielectric material. Without undue experimentation, the appropriate voltage can be applied to cause piezoelectric buzzing to occur. The rate of binding of a protein to the surface or another protein in a microtiter plate or on a microarray chip is accelerated by at least a factor of two, preferably a factor of ten or more (Sizto & Gallup, U.S. Pat. No. 4,575,485; Wohlstadter et al. U.S. Pat. No. 6,413,783). Subsequently, an immunoassay assay can be carried out (the leads to the dielectric are removed if necessary to prevent microwave interferences or sparking). The ceramic dielectric becomes the target of microwave heating, and heating accelerates the signaling reaction (chemiluminescence, for example).

REFERENCES

Below is a list of publications cited herein:

Dielectric Heating/Materials and Microwave Chemistry
ASTM Committee E20 on Temperature Measurement (1993) ASTM, Philadelphia.
Boon, M. E. & Kok, L. P. (1989) in Microwave Cookbook of Pathology, Coulomb Press, Leiden.
Borman, S. (2001) Chem. Engin. News 79 (35) 49-58.
Bose, A. K. et al. (1997) CHEMTECH 27(9), 18-25.
Bradley, D. (2001) Modern Drug Discovery 4(8), 32-36.
Bram, G., Loupy, A., Majdoub, M., Gutierrez, E., & Ruiz-itky, E. (1990) Tetrahedron 46, 5167.
Bram, G., Loupy, A., Majdoub, M., and Petit, A. (1991) Chem. Ind. 396.
Buffler, C. R. & Risman, P. O. (1996) Mat. Res. Soc. Symp. Proc. 430, 85.
Ewart, T. G. & Gavin, G. T. (1999) Nanoparticles Biosensor, U.S. Pat. No. 5,922,537.
Gabriel, C., Gabriel, S., Grant, E. H., Halstead, B. S. J., Mingos, D. M. P. (1998) Chem. Soc. Rev. 27, 213-224.
Holworth, A. et al. Ind. Eng. Chem. Res. (1998) 37, 2701.
Huhmer, A. F. R. and Landers, J. P (2000) Anal. Chem. 72, 5507-5512.
Jin, Q. et al. (1999) Trends Anal. Chem. 18, 479-484.
Kappe, C. O. (2001) American Laboratory 23, 13-19.
Kidwai, M., Kohli, S., Saxena, R. K., Gupta, R., and Bardoo, S. (1998) Ind. J. Chem. 37B, 963.
Kreider, K. G. (1989) Thin Film Thermocouples For High Temperature Measurement. NIST, Springfield, Va.
Kubrakova, I. V. (2000) J. Anal. Chem. 55, 1113-1122.
Laszlo, T. S. (1980) The Physics Teacher, November, 570-579.
Lew, A., Krutzik, P. O., Hart, M. E., & Chamberlain, A. R. (2002) J. Comb. Chem. 4, 95-105.
Mingos, D M P & Baghurst, D R (1991) Chem. Soc. Rev. 20, 1-47.
Nesatyy, V. J., Dacanay, A., Kelly, J. F., & Ross, N. W. (2002) Rapid Commun. Mass Spectrom. 16, 272-280.
Roussy, G. & Pearce, J. A. Foundations and Industrial Applications of Microwave and Radio Frequency Fields. Physical and Chemical Processes. Wiley & Sons (1995) New York.
Schultz, P. G., Xiang, X., & Goldwasser, I. (1999) Combinatorial Synthesis of Novel Materials, U.S. Pat. No. 5,985,356.
Slyanev, M. N. (2001) Anal. Chem. 73, 4037-4044.
Varma, R. (2001) AMPERE Newsletter, Issue 29, ISSN 1361-8598.
Wathey, B., Tierney, J., Lidstrom, P., & Westman, J. (2002) Drug Discov. Today 7, 373-380.
Yang, P. et al. (1998) Science 282, 2244.
Zlotorzynski, A. Crit. Rev. Anal. Chem. (1995) 25, 43.

Molecular Imprinting, Zeolites, and other Binding Molecules
Borchart, A. & Still, W. C. (1994) J. Am. Chem. Soc. 116, 373.
Breslow, R. et al. (1983) J. Am. Chem. Soc. 105, 2739.
Burow, M. & Minoura, N. (1996) Biochem. Biophys. Res. Commun. 227, 419.
Bystrom, S. E. et al. (1993) 115, 2081.
Dai, S. et al. (1999) Angew. Chem. Int. Ed. 38, 1235.
Dickert, F L & Thierer S (1996) Adv. Mater. 8, 987.
Fleischer, C. T. & Boos, K.-S. (2001) American Laboratory, May, 20-25.
Glad et al. (1985) J. Chromatogr. 347, 11.
Gu, W. et al. (1999) J. Am. Chem. Soc. 121, 9467.
Jansen, J. C. et al. (1994) in Advanced Zeolite Science and Applications, J. C. Jansen et al., eds., pp. 215-250, Elsevier, N.Y.
Jones, K. D. (2001) IVD Technology 7(6) 50-54.
Kempe et al. (1995) J. Mol. Recog. 8, 35.
Krishnan, T. R. & Ibraham, I. (1994) J. Pharm. Biomed. Anal. 12, 287-294.
Leonhardt, A. & Mosbach, K. (1987) Reactive Polymers 6, 285.
Makote, R. & Collinson, M. M. (1998) Chem. Commun. 3, 425.
Mathew-Krotz, J. & Shea, K. J. (1995) J. Am. Chem. Soc. 118, 8134.
Maugh, T. H. (1984) Science 223, 269.
Maugh, T. H. (1983a) Science 221, 351.
Maugh, T. H. (1983b) Science 222, 151.
Norrlow, O. et al. (1984) 299, 29.
O'Shannessy et al. (1989a) Anal. Biochem. 177, 144.
O'Shannessy et al. (1989b) J. Chromatogr. (1989b) 470, 391.
Rouhi, A. M. (2000) Chem. Eng. News 78 (34) 40.
Shi et al. (1999) Nature 398, 593.
van Bekkum, H. et al. (1994) in Advanced Zeolite Science and Applications, J. C. Jansen et al., eds., pp. 509-542, Elsevier, N.Y.

Microchips/Microarrays/Microtiter Plates and Assays
Cooper, C. S. (2001) Breast Cancer Res. 3, 158-175.
Lennon, G. G. (2000) Drug Discov. Today 5, 59-66.
Pasinetti, G. M. (2001) J. Neurosci. Res. 65, 471-476.
Draghici, S. et al. (2001) Curr. Opin. Drug Discov. Dev. (2001) 4, 332-337.
Schmalzing, D. et al. (2000) Electrophoresis 21, 3919-3930.
Zubritsky, E. (2001) Modern Drug Discov., May issue, 59-71.
Robinson, J. K. (2000) American Laboratory, December, 28-34.
Sizto, N. C. & Gallup, C. (1986) Ultrasonic Enhanced Immuno-Reactions, U.S. Pat. No. 4,575,485.
Wohlstadter, J. N., Wilbur, J., Sigal, G., Martin, M., Fischer, A., Helms, L. R., & Darvari, R. (2002) U.S. Pat. No. 6,413,783).

Practical Applications in Biomedicine

Bowie, A. R., Sanders, M. G., & Worsfold, P. J. (1996) J. Biolumin. Chemilumin. 11, 61-90.

Johnson, B. (1999) The Scientist 13, 16.

Roda, A., Pasini, P., Guardigli, M., Baraldini, M., Musiani, M., & Mirasoli, M. (2000) Fresenius J. Anal. Chem. 366, 752-9.

Wood, W. G. (1984) J. Clin. Chem. Clin. Biochem. 22, 905-918.

Folkman, J. (1997) EXS 79, 1-8.

Saaristo, A., Karpanen, T., and Alitalo, K. (2000) Oncogene 19, 6122-6129.

Sidransky, D. (1997) Science 278, 1054-1058.

Abati, A. & Liotta, L. A. (1996) Cancer 78, 1-3.

Marx, J. (2000) Science 289, 1670-1672.

Latchman, D. S. (1995) PCR Applications in Pathology. Principles and Practice. NY, Oxford Univ. Press.

Freeman, W. M., Walker, S. J., & Vrana, K. E. (1999) BioTechniques 26, 112-125.

Seiden, M. L. & Sklar, J. L. (1996) in Important Advances In Oncology, D. T. DeVita, ed., Philadelphia, Lippincott-Raven.

Schena, M., Shalon, D., Davis, R. W., & Brown, P. O. (1995) Science 270, 467-470.

Harkin, D. P. (2000) Oncologist 5, 501-7.

Kricka, L. J. (1999) Clin. Chem. 45, 453-8.

Leitzel, K., Lieu, B., Curley, E., Smith, J., Chinchilli, V., Rychlik, W., & Lipton, A. (1998) Clin. Cancer Res. 4, 3037-3043.

Price, C. P. & Newman, D. J. (1997) Principles and Practice of Immunoassay 2nd Ed. Macmillan, London.

Wild, D. (2000) Immunoassay Handbook $2^{nd}$ Ed. Macmillan, London.

Microwave Chemistry/Chemical Microarrays

Dolle, R. E. (2000) J. Comb. Chem. 2, 383-433.

Fodor, S. P. A., Rava, R. P., Huang, X. C., Pease, A. C., Holmes, C. P., & Adams, C. L. (1993) Nature 364(6437), 555-556.

Gallop, M. A., Barrett, R. W., Dower, W. J., Fodor, S. P. A., & Gordon, E. M. (1994) J. Med. Chem. 37, 1233-1251.

Gordon, E. M., Barrett, R. W., Dower, W. J., Fodor, S. P. A., & Gallop, M. A. (1994) J. Med. Chem. 37, 1385-1401.

Hilpert, K., Hansen, G., Wessner, H., Kuttner, G., Welfle, K., Seifert, M., & Hohne, W. (2001) Protein Engineering 14, 803-806.

Jacobs, J. W. & Fodor, S. P. A. (1994) Trends Biotechnol. 12, 19-26.

Kramer, A. & Schneider-Mergener (1998) Methods Mol. Biol. 87, 25-39.

Korbel, G. A., Lalic, G., & Shair, M D (2001) J. Am. Chem. Soc. 123, 361-362.

Hergenrother, P. J., Depew, K. M., & Schreiber, S. L. J. Am. Chem. Soc. (2000) 122, 7849-7850.

Kappe, C. O. (2002) Curr. Opin. Chem. Biol. 6, 314-320.

Lew, A., Krutzik, P. O., Hart, M. E., & Chamberlain, A. R. (2002) J. Combinatorial Chemistry 4, 95-105.

Lidstrom, P., Tierney, P., Walthey, B., & Westman, J. (2001) Tetrahedron 57, 9225-9283.

MacBeath, G., Koehler, A. N., & Schreiber, S. L. (1999) J. Am. Chem. Soc. 121, 7967-7968.

Wathey, B., Tierney, J., Lidstrom, P., & Westman, J. (2002) Drug Discovery Today 7, 373-380.

Yu, H.-M., Chen, S.-T., & Wang, K.-T. (1992) 57, 4781-4784.

All publications and patents mentioned in this specification are herein incorporated by reference to the same extent as if each individual publication or patent application was specifically and individually indicated to be incorporated by reference in the entirety.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for accelerating a biospecific interaction of a reactant in an aqueous or organic solution proximal to a surface, said method comprising:
    (a) contacting a composite with said reactant, said composite comprising: (i) a solid material susceptible to microwave heating attached to (ii) a surface molecule,
    (b) applying an electromagnetic field of a wavelength of between 1 cm and 100 m to said composite resulting in direct microwave heating of said solid material, without substantially heating said aqueous or organic solution so that the temperature of the solid material is higher than that of the surface molecule, and
    (c) allowing said composite to react with said reactant, wherein the reactant is thermally proximal to the composite, whereby the reactant is heated by heat transfer from the heated solid material and binds to the surface molecule at a greater rate than without heating from the heated soild material, thereby accelerating said biospecific interaction.

2. The method of claim 1, further comprising the step of measuring the extent or rate of said biospecific interaction.

3. The method of claim 1, further comprising the steps of:
    (d) contacting said composite with one or more additional reactant(s),
    (e) allowing said additional reactant(s) to react in one or more biospecific interactions, and
    (f) measuring the extent or rate of one or more of said biospecific interactions.

4. The method of claim 1, further comprising the steps of:
    (d) contacting said composite with one or more additional reactant(s) for one or more further biospecific interactions,
    (e) applying an electromagnetic field to said composite, said electromagnetic field being sufficient to result in microwave heating of said solid material, said additional reactant(s) being heated by heat transfer from said heated solid material,
    (f) allowing said heated additional reactant(s) to react, thereby accelerating one or more of said further biospecific interactions, and
    (g) measuring the extent or rate of one or more of said further biospecific interactions.

5. The method of claim 1, further comprising the steps of:
    (d) measuring the extent or rate of the reaction,
    (e) contacting said composite with one or more additional reactant(s)
    (f) applying an electromagnetic field to said composite, said electromagnetic field being sufficient to result in microwave heating of said solid material, said additional reactant(s) being heated by heat transfer from said heated solid material,
    (g) allowing one or more of said heated second reactant(s) to react, thereby accelerating one or more of said further biospecific interactions, and
    (h) measuring the extent or rate of one or more of said further biospecific interactions.

6. The method of claim 1, wherein said reactant is selected from the group consisting of an amino acid, a protein, a peptide, an oligonucleotide, and a polynucleotide.

7. The method of claim 1, wherein said biospecific interaction is a noncovalent adsorption reaction.

8. The method of claim 1, wherein said reactant is an amino acid.

9. The method of claim 1, where said biospecific interaction is a covalent conjugation reaction.

10. The method of any one of claims 1, 3, 4, or 5 wherein one or more of said biospecific interactions is selected from the group consisting of: a chemiluminescent reaction, a reaction resulting in a change in visible or ultraviolet color, and a reaction involving a change in fluorescent properties.

11. The method of any one of claims 1, 3, 4, or 5, wherein one or more of said reactant(s) is a product of an enzymatic reaction.

12. The method of claim 1, wherein said solid material susceptible to microwave heating comprises a dielectric material, and wherein said application of said electromagnetic field additionally results in dielectric heating.

13. The method of claim 1, wherein said solution is an aqueous solution and said solid material is more susceptible to microwave heating than water.

14. A method for a biospecific interaction of a biologically active reactant in an aqueous or organic solution proximal to a surface, said method comprising:
    (a) contacting a composite with said reactant, said composite comprising: (i) a solid material susceptible to microwave heating attached to (ii) a surface molecule,
    (b) applying an electromagnetic field of a wavelength of between 1 cm and 100 m to said composite resulting in direct microwave heating of said solid material without substantially heating said aqueous or organic solution so that the temperature of the solid material is higher than that of the surface molecule, and
    (c) allowing said composite to react with said reactant, wherein the reactant is thermally proximal to the composite so that the heated solid material heats the thermally proximal reactant, whereby the reactant maintains biological activity and binds to the surface molecule at a greater rate than without heating from the heated solid material, thereby accelerating said biospecific interaction while maintaining the biological activity of the reactant.

15. The method of claim 14, wherein said solution is an aqueous solution and said solid material is more susceptible to microwave heating than water.

* * * * *

```
                        SEQUENCE LISTING

<160> NUMBER OF SEQ ID NOS: 2

<210> SEQ ID NO 1
<211> LENGTH: 10
<212> TYPE: PRT
<213> ORGANISM: Homo sapiens

<400> SEQUENCE: 1

Glu Gln Lys Leu Ile Ser Glu Glu Asp Leu
 1               5                  10

<210> SEQ ID NO 2
<211> LENGTH: 10
<212> TYPE: PRT
<213> ORGANISM: Homo sapiens

<400> SEQUENCE: 2

Glu Gln Lys His Ile Ser Glu Glu Asp Leu
 1               5                  10
```